United States Patent
Yokono et al.

(10) Patent No.: US 12,410,488 B2
(45) Date of Patent: Sep. 9, 2025

(54) METHOD FOR DETECTING CORONAVIRUS (SARS-CoV-2)

(71) Applicant: EIKEN KAGAKU KABUSHIKI KAISHA, Tokyo (JP)

(72) Inventors: Kota Yokono, Tochigi (JP); Machiko Yamamoto, Tochigi (JP); Syota Yuki, Tochigi (JP); Ai Fukaya, Tochigi (JP); Yutaka Kubota, Tochigi (JP)

(73) Assignee: EIKEN KAGAKU KABUSHIKI KAISHA, Tokyo (JP)

( * ) Notice: Subject to any disclaimer, the term of this patent is extended or adjusted under 35 U.S.C. 154(b) by 570 days.

(21) Appl. No.: 17/905,497

(22) PCT Filed: Mar. 3, 2021

(86) PCT No.: PCT/JP2021/008261
§ 371 (c)(1),
(2) Date: Sep. 1, 2022

(87) PCT Pub. No.: WO2021/177372
PCT Pub. Date: Sep. 10, 2021

(65) Prior Publication Data
US 2023/0125553 A1    Apr. 27, 2023

(30) Foreign Application Priority Data

Mar. 5, 2020 (JP) ................. 2020-038195
Nov. 18, 2020 (JP) ................. 2020-191630

(51) Int. Cl.
| *C12Q 1/68* | (2018.01) |
| *C12Q 1/6844* | (2018.01) |
| *C12Q 1/6888* | (2018.01) |
| *C12Q 1/70* | (2006.01) |

(52) U.S. Cl.
CPC .......... *C12Q 1/701* (2013.01); *C12Q 1/6844* (2013.01); *C12Q 1/6888* (2013.01); *C12Q 2600/16* (2013.01)

(58) Field of Classification Search
None
See application file for complete search history.

(56) References Cited

U.S. PATENT DOCUMENTS

| 2021/0291165 A1* | 9/2021 | Rothberg | ......... G01N 33/54388 |
| 2021/0292825 A1* | 9/2021 | Rothberg | ............... B01L 3/5029 |
| 2021/0340636 A1* | 11/2021 | Brambati | ................ C12Q 1/701 |
| 2022/0010386 A1* | 1/2022 | Kemble | ................ C12Q 1/6846 |

FOREIGN PATENT DOCUMENTS

| JP | 2001-242169 A | 9/2001 | |
| JP | 2004-283161 A1 | 10/2004 | |
| JP | 2018-121607 A | 8/2018 | |
| WO | 00/028082 A1 | 5/2000 | |
| WO | 01/083817 A1 | 11/2001 | |
| WO | 02/024902 A1 | 3/2002 | |
| WO | 2016/098892 A1 | 6/2016 | |
| WO | WO-2021236987 A2 * | 11/2021 | ............. C12N 15/11 |
| WO | WO-2021245708 A1 * | 12/2021 | ............. C12Q 1/701 |

OTHER PUBLICATIONS

International Bureau of the Patent Cooperation Treaty, Transmittal of Translation of the International Preliminary Report on Patentability issued in PCT/JP2021/008261, Sep. 15, 2022, pp. 1-5.
Chan, et al., "A familial cluster of pneumonia associated with the 2019 novel coronavirus indicating person-to-person transmission: a study of a family cluster", The Lancet, Jan. 24, 2020, pp. 514-523, vol. 395(10223).
National Institute of Infectious Disease in Japan, "Pathogen Detection Manual 2019-nCoV Ver.2.7", https://www.niid.go.jp/niid/images/lab-manual/2019-nCoV20200225.pdf, Feb. 25, 2020, pp. 1-18, English translated.
Centers for Disease Control and Prevention, "CDC Tests for COVID-19", https://www.cdc.gov/coronavirus/2019-ncov/about/testing.html, Feb. 15, 2020, p. 1.
Yang, W. et al., "Rapid Detection of SARS-CoV-2 Using Reverse transcription RT-LAMP method", medRxiv, https://www.medrxiv.org/content/10.1101/2020.03.02.20030130v2, Mar. 3, 2020, pp. 1-26.
Yu, L. et al., "Rapid colorimetric detection of COVID-19 coronavirus using a reverse transcriptional loop-mediated isothermal amplification (RT-LAMP) diagnostic platform: iLACO", medRxiv, https://www.medrxiv.org/content/10.1101/2020.02.20.20025874v1, Feb. 24, 2020, pp. 1-20.
Zhang, Y., et al., "Rapid Molecular Detection of SARS-CoV-2 (COVID-19) Virus RNA Using Colorimetric LAMP", medRxiv, https://www.medrxiv.org/content/10.1101/2020.02.26.20028373v1, Feb. 29, 2020, pp. 1-15.
"Definition: Severe acute respiratory syndrome coronavirus 2 isolate Wuhan-Hu-1, complete genome", https://www.ncbi.nlm.nih.gov/nuccore/I79817243I?sat=48&satkey=31053637, Feb. 11, 2020, pp. 1-11.
Patent Cooperation Treaty, International Search Report issued in PCT/JP2021/008261, May 18, 2021, pp. 1-3.

* cited by examiner

*Primary Examiner* — Aaron A Priest
(74) *Attorney, Agent, or Firm* — Pillsbury Winthrop Shaw Pittman LLP

(57) ABSTRACT

Disclosed are oligonucleotide primers that hybridize specifically with any base sequence designed from the base sequences of the N gene, RNA-dependent RNA polymerase gene, M gene, and S gene of SARS-CoV-2, a nucleic acid amplification method using said primers, a test method for SARS-CoV-2 infection by detection of nucleic acid amplification, and a COVID-19 test kit.

16 Claims, No Drawings
Specification includes a Sequence Listing.

METHOD FOR DETECTING CORONAVIRUS (SARS-CoV-2)

RELATED PATENT APPLICATIONS

This application is based on and claims the benefit of priority from International Application No. PCT/JP2021/008261, filed on Mar. 3, 2021, which claims priority to Japanese Patent Application No. 2020-038195, filed on Mar. 5, 2020, and claims priority to Japanese Patent Application No. 2020-191630, filed on Nov. 18, 2020, the contents of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Aug. 23, 2022, is named "051723-0571005_SequenceListing.txt" and is 46.2 KB in size.

TECHNICAL FIELD

The present invention relates to a method for detecting a new coronavirus (SARS-CoV-2) discovered in 2019, and more specifically to a method for assisting diagnosis of acute respiratory disease (COVID-19) due to the new 2019 coronavirus utilizing a highly sensitive method for detecting genes.

BACKGROUND ART

Acute respiratory disease (COVID-19) due to the new 2019 coronavirus was reported in December 2019 as outbreaks of patients with pneumonia of unknown causes in Wuhan City, Hubei Province, China. The cause was confirmed to be a new coronavirus on Jan. 7, 2020, and the following week, infected persons were confirmed in a plurality of countries in addition to China. As of the end of January, the number of infected persons exceeded 10,000, but the spread of the infection did not stop, and the World Health Organization (WHO) declared a Public Health Emergency of International Concern (PHEIC) on January 31st.

The main clinical symptoms of COVID-19 are fever, cough, and general malaise. When it becomes severe, it causes pneumonia or dysfunction of the lungs, the heart, and the kidneys, which may lead to death. Although the mortality is about 3% which is lower than that of the SARS epidemic from 2002 to 2003, the number of infected persons is much higher than that of SARS. Therefore, the death toll is higher than that of the SARS epidemic.

The new virus (SARS-CoV-2) that causes COVID-19 is a betacoronavirus similar to the SARS coronavirus or MERS coronavirus. The genes of the new virus consist of a positive strand of single-stranded RNA and have a length of about 30,000 bases (GENBANK Accession No. MN908947).

The entire sequence of SARS-CoV-2 was determined and published about 1 month after the first report of the outbreak of pneumonia in patients. Based on the sequence, methods for detecting SARS-CoV-2 through RT-PCR have been developed (Non Patent Literature 1 and others).

However, since these detection methods were developed in a short period of time, some of them have problems in detection accuracy. For example, it has been announced that some of test kits developed by The Centers for Disease Control and Prevention (CDC) have defects (refer to Non Patent Literature 2). In addition, the number of tests required is also enormous due to the rapid spread of infection. For these reasons, a faster and more accurate method for detecting SARS-CoV-2 is required.

CITATION LIST

Non Patent Literature

[Non Patent Literature 1] National Institute of Infectious Disease: Pathogen Detection Manual 2019-nCoV Ver.2.7 (edited on Feb. 25, 2020), Internet <URL: https://www.niid.go.jp/niid/images/lab-manual/2019-nCoV20200225.pdf>

[Non Patent Literature 2] CDC Tests for COVID-19, retrieved on Feb. 18, 2020, Internet <URL: https://www.cdc.gov/coronavirus/2019-ncov/about/testing.html>

SUMMARY OF INVENTION

Technical Problem

An object of the present invention is to detect SARS-CoV-2, which is a pathogenic virus of COVID-19, with high sensitivity for diagnosis of COVID-19.

Solution to Problem

The present inventors have conducted extensive studies to solve the above-described problem, and as a result, they have found that SARS-CoV-2 can be detected with high sensitivity by producing an oligonucleotide primer that is selectively hybridized with a sequence specific to SARS-CoV-2 and amplifying the sequence specific to SARS-CoV-2 through a LAMP method, thus leading to realization of the present invention.

That is, the present invention has the following configuration.

[1] A primer set for detecting SARS-CoV-2 virus through amplification by a LAMP method, wherein the primer set consists of at least one designed from regions (a) and (b):
(a) a region from a 28976th base to a 29211th base of SEQ ID NO: 1; and
(b) a region from a 15394th base to a 15595th base of SEQ ID NO: 1.

[2] A primer set for detecting SARS-CoV-2 virus through amplification by a LAMP method, wherein the primer set consists of at least one selected from the group consisting of (a1) and (b1):
(a1) a primer set consisting of an F3 primer consisting of SEQ ID NO: 2, a B3 primer consisting of SEQ ID NO: 3, an FIP primer consisting of SEQ ID NO: 4, and a BIP primer consisting of SEQ ID NO: 5; and
(b1) a primer set consisting of an F3 primer consisting of SEQ ID NO: 8, a B3 primer consisting of SEQ ID NO: 9, an FIP primer consisting of SEQ ID NO: 10, and a BIP primer consisting of SEQ ID NO: 11.

[3] A primer set for detecting SARS-CoV-2 virus through amplification by a LAMP method, wherein the primer set consists of at least one selected from the group consisting of (a2) and (b2):
(a2) an LF primer consisting of SEQ ID NO: 6 and an LB primer consisting of SEQ ID NO: 7 in addition to the primer set of (a1) of [1]; and (b2) an LF primer consisting of SEQ ID NO: 12 and an LB primer consisting of SEQ ID NO: 13 in addition to the primer set of (b1) of [1].

[4] A method for detecting SARS-CoV-2 virus, comprising performing an amplification reaction through a LAMP method using the primer set of any one of [1] to [3].

[5] A method for testing for COVID-19, comprising detecting amplification of a target nucleic acid region of SARS-CoV-2 virus using the primer set of any one of [1] to [3] to test for presence or absence of infection with SARS-CoV-2 virus.

[6] A kit comprising the primer set of any one of [1] to [3] in a method for diagnosing COVID-19.

[7] A primer set for detecting SARS-CoV-2 virus through amplification by a LAMP method, wherein the primer set consists of at least one designed from regions (c) and (d):

(c) a region from a 26767th base to a 26977th base of SEQ ID NO: 1; and (d) a region from a 24660th base to a 24916th base of SEQ ID NO: 1.

[8] A primer set for detecting SARS-CoV-2 virus through amplification by a LAMP method, wherein the primer set consists of at least one selected from the group consisting of (c1) and (d1):

(c1) a primer set consisting of an F3 primer consisting of SEQ ID NO: 14, a B3 primer consisting of SEQ ID NO: 15, an FIP primer consisting of SEQ ID NO: 16, and a BIP primer consisting of SEQ ID NO: 17; and (d1) a primer set consisting of an F3 primer consisting of SEQ ID NO: 21, a B3 primer consisting of SEQ ID NO: 22, a B4 primer consisting of SEQ ID NO: 23, an FIP primer consisting of SEQ ID NO: 24, and a BIP primer consisting of SEQ ID NO: 25.

[9] A primer set for detecting SARS-CoV-2 virus through amplification by a LAMP method, wherein the primer set consists of at least one selected from the group consisting of (c2) and (d2):

(c2) a primer set consisting of an F3 primer consisting of SEQ ID NO: 14, a B3 primer consisting of SEQ ID NO: 15, an FIP primer consisting of SEQ ID NO: 16, a BIP primer consisting of SEQ ID NO: 17, an LF primer consisting of SEQ ID NO: 18, and an LB primer consisting of SEQ ID NO: 19; and (d2) a primer set consisting of an F3 primer consisting of SEQ ID NO: 21, a B3 primer consisting of SEQ ID NO: 22, a B4 primer consisting of SEQ ID NO: 23, an FIP primer consisting of SEQ ID NO: 24, a BIP primer consisting of SEQ ID NO: 25, an LF primer consisting of SEQ ID NO: 26, and an LB primer consisting of SEQ ID NO: 27.

[10] A kit for detecting SARS-CoV-2 virus through amplification by a LAMP method, comprising the primer set of any one of [7] to [9]; and a fluorescence labeling probe.

[11] The kit of [10], wherein the primer set is a primer set of (c1) or (c2), and the fluorescence labeling probe is a probe consisting of SEQ ID NO: 20.

[12] The kit of [10], wherein the primer set is a primer set of (d1) or (d2), and the fluorescence labeling probe is a probe consisting of SEQ ID NO: 28.

[13] The kit of any one of [10] to [12], which is used for testing for COVID-19.

[14] A method for detecting SARS-CoV-2 virus, comprising performing an amplification reaction through a LAMP method using the primer set of any one of [7] to [9] or the kit of any one of [10] to [13].

[15] A method for testing for COVID-19, comprising detecting amplification of a target nucleic acid region of SARS-CoV-2 virus using the primer set of any one of [7] to [7] or the kit of any one of [10] to [13] to test for presence or absence of infection with SARS-CoV-2 virus.

Advantageous Effects of Invention

According to the present invention, SARS-CoV-2 can be promptly detected with high sensitivity by producing an oligonucleotide primer that is selectively hybridized with a sequence specific to SARS-CoV-2 and amplifying the sequence specific to SARS-CoV-2 through a LAMP method.

DESCRIPTION OF EMBODIMENTS

Examples of samples used in the present invention include specimens, such as sputum, bronchoalveolar lavage fluid, nasal mucus, nasal suction fluid, nasal lavage fluid, nasal swabs, pharyngeal swabs, mouthwash, saliva, blood, serum, plasma, cerebrospinal fluid, urine, feces, and tissue, derived from humans or other animals suspected of being infected with SARS-CoV-2 virus. In addition, cells used in infection experiments or the like or their culture solutions, or specimens derived from living bodies or specimens containing viruses isolated from cultured cells or the like can also be used as samples. These samples may be subjected to pretreatment such as separation, extraction, concentration, and purification.

Amplification of nucleic acids contained in a sample is achieved by a loop-mediated isothermal amplification method (WO 00/28082) called a LAMP method that is a nucleic acid amplification method which was developed by Notomi et al. and does not require temperature control indispensable for a PCR method. This method is a nucleic acid amplification method which enables an isothermal complementary strand synthesis reaction by combining primers which anneal their own 3' terminals to template nucleotides to serve as starting points for complementary strand synthesis and are annealed to loops formed at this time. In addition, in the LAMP method, since the 3' terminal of a primer is always annealed to a region derived from a sample, a check mechanism due to a complementary bond of sequences functions repeatedly. As a result, the LAMP method enables a nucleic acid amplification reaction with high sensitivity and high specificity.

Regarding oligonucleotide primers used in a LAMP method, there are at least 4 types of primers recognizing a sequence in a total of 6 regions of the sequence of a template nucleic acid, that is, regions F3c, F2c, and F1c from the 3' terminal side and regions B3, B2, and B1 from the 5' terminal side, which are called a forward inner primer, a backward inner primer, a forward outer primer, and a backward outer primer. In addition, complementary sequences of F1c, F2c, and F3c are respectively called F1, F2, and F3, and complementary strands of B1, B2, and B3 are respectively called B1c, B2c, and B3c. An inner primer is an oligonucleotide which recognizes a "specific nucleotide sequence region" on a target base sequence, has a sequence, providing a starting point for synthesis, at the 3' terminal, and simultaneously has a sequence complementary to an arbitrary region of a nucleic acid synthesis reaction product with this primer as a starting point, at the 5' terminal. Here, a primer containing a "sequence selected from F2" and a "sequence selected from F1c" is called a forward inner primer (hereinafter, an FIP primer), and a primer containing a "sequence selected from B2" and a "sequence selected from B1c" is called a backward inner primer (hereinafter, a BIP primer). On the other hand, an outer primer is an oligonucleotide which recognizes a "specific nucleotide sequence region" present on the 3' terminal side of a "specific nucleotide sequence region" on a target sequence and has a sequence providing a starting point for synthesis. Here, a primer containing a "sequence selected from F3" is called a forward outer primer (hereinafter, an F3 primer), and a primer containing a "sequence selected from B3" is called a backward outer primer (hereinafter, a B3 primer). Here, F in each primer represents a primer which complementarily binds to a sense strand of a target sequence and provides a starting point for synthesis, while B represents a primer which complementarily binds to an antisense strand of a target sequence and provides a starting point for synthesis. Here, the length of an oligonucleotide used as a primer is greater than or equal to 10 bases and preferably greater than or equal to 15 bases, and may be either chemically synthesized or natural. Each primer may be a single oligonucleotide or may be a mixture of a plurality of oligonucleotides.

In a LAMP method, in addition to the inner primers and the outer primers, another primer, that is, a loop primer, can be used. A loop primer is a primer having a sequence complementary to a sequence of a single-stranded portion of a loop structure on the 5' terminal side of a dumbbell structure. When this primer is used, the number of starting points for nucleic acid synthesis increases, whereby the reaction time can be reduced and the detection sensitivity can be increased (WO 02/024902). A sequence of a loop primer may be a sequence of a target gene or selected from a complementary strand thereof, or may be other sequences as long as it is complementary to the above-described sequence of a single-stranded portion of a loop structure on the 5' terminal side of a dumbbell structure. In addition, the loop primer may be one kind or two or more kinds, and is called a forward loop primer (hereinafter, LF) and a backward loop primer (hereinafter, LB) in the present specification.

In a case where a gene of a single-stranded RNA virus is detected through amplification by a LAMP method, an outer primer can be further added to increase the efficiency of a reverse transcription reaction in an initial stage of the amplification reaction. Since SARS-CoV-2 is a plus-strand single-stranded RNA virus, an outer primer (B4 primer) may be added to the downstream side of a B3 primer.

SARS-CoV-2 is an RNA virus. In a LAMP method, in a case where RNA is used as a template, a nucleic acid amplification reaction can similarly proceed by adding a reverse transcriptase to a reaction solution in a case where DNA is used as a template (RT-LAMP method).

The present inventors have conducted extensive studies on base sequences of primers in a LAMP method capable of promptly amplifying a sequence specific to SARS-CoV-2, and a combination thereof, and as a result, they have designed primer sets from an N gene region and an RNA-dependent RNA polymerase (RdRP) gene region of a sequence (SEQ ID NO: 1) of SARS-CoV-2. That is, the present invention is a primer set consisting of at least one designed from an N gene region (a region from a 28976th base to a 29211th base of SEQ ID NO: 1) and an RNA-dependent RNA polymerase (RdRP) gene region (a region from a 15394th base to a 15595th base of SEQ ID NO: 1) of a sequence (SEQ ID NO: 1) of SARS-CoV-2. The present invention is a primer set consisting of F3, B3, FIP, and BIP and designed as being a primer set comprising at least one selected from the following two sets a and b. In addition, the present invention is a primer set comprising an LF primer and an LB primer and comprising at least one selected from the following two sets a and b.

TABLE 1

| Primer name | | Base sequence | SEQ ID NO. |
|---|---|---|---|
| Primer set a (N gene) | F3 | TCTGGTAAAGGCCAACAAC | 2 |
| | B3 | GCTGAAGCGCTGG | 3 |
| | FIP | AGTACGTTTTTGCCGAGGC-AAGGCCAAACTGTCACT | 4 |
| | BIP | GTAACACAAGCTTTCGGCAG-ATTAGTTCCTGGTCCCCAA | 5 |
| | LF | AAGCCTCAGCAGCAGAT | 6 |
| | LB | TCCAGAACAAACCCAAGG | 7 |
| Primer set b (RdRP) | F3 | TTCTATAGATTAGCTAATGAGTGT | 8 |
| | B3 | ACTTATCGGCAATTTTGTTACC | 9 |
| | FIP | GAGGTTCCACCTGGTTTAACATAT-CTCAAGTATTGAGTGAAATGGT | 10 |
| | BIP | CAGGAGATGCCACAACTGCTTAT-AGATAAAAGTGCATTAACATTGG | 11 |
| | LF | GAACCGCCACACATGACC | 12 |
| | LB | CATTTGTCAAGCTGTCACGG | 13 |

In addition, the present inventors have conducted extensive studies on base sequences of primers in a LAMP method capable of promptly amplifying a base sequence specific to SARS-CoV-2, and a combination thereof, and as a result, they have designed primer sets from an M gene region and an S gene region of a sequence (SEQ ID NO: 1) of SARS-CoV-2. That is, the present invention is a primer set consisting of at least one designed from an M gene region (a region from a 26767th base to a 26977th base of SEQ ID NO: 1) and S gene region (a region from a 24660th base to a 24916th base of SEQ ID NO: 1) of a sequence (SEQ ID NO: 1) of SARS-CoV-2. The present invention is a primer set which consists of F3, B3 (or B3 and B4), FIP, and BIP and consists of at least one selected from the following two sets c and d. In addition, the present invention is a primer set comprising an LF primer and an LB primer and comprising at least one selected from the following two sets c and d.

TABLE 2

| Primer name | | Base sequence |
|---|---|---|
| Primer set c (M gene) | F3 | TCGCAATGGCTTGTCTTG (SEQ ID NO: 14) |
| | B3 | GCAATACGAAGATGTCCACG (SEQ ID NO: 15) |
| | FIP | CGTACGCGCAAACAGT-GGCTTGATGTGGCTCAG (SEQ ID NO: 16) |
| | BIP | CGTTCCATGTGGTCATTCA-TAGAAGCGGTCTGGTCAG (SEQ ID NO: 17) |
| | LF | GAAAGAAGCAATGAAGTAGC (SEQ ID NO: 18) |
| | LB | GAAACTAACATTCTTCTCAACG (SEQ ID NO: 19) |
| Primer set d (S gene) | F3 | TACTTGGACAATCAAAAAGAGTT (SEQ ID NO: 21) |
| | B3 | GTCTGTAGTAATGATTTGTGGTTC (SEQ ID NO: 22) |
| | B4 | TGTCTGTAGTAATGATTTGTGG (SEQ ID NO: 23) |
| | FIP | CTTTTCTTGTGCAGGGACA-CTATCATCTTATGTCCTTCCCTC (SEQ ID NO: 24) |

TABLE 2-continued

| Primer name | Base sequence |
|---|---|
| BIP | TCACAACTGCTCCTGCC-TGAAACAAAGACACCTTCACG (SEQ ID NO: 25) |
| LF | ACATGCAAGAAGACTACACCA (SEQ ID NO: 26) |
| LB | GATGGAAAAGCACACTTTCCT (SEQ ID NO: 27) |

Furthermore, the present invention is a kit comprising the above-described primer set c or d and a fluorescence labeling probe. A probe for the primer set c is a probe consisting of SEQ ID NO: 20, and a probe for the primer set d is a probe consisting of SEQ ID NO: 28. Cytosine bases at the 3' terminals of these probes are fluorescently labeled with BODIPY (registered trademark) FL dye. These probes are Q-probes. That is, when the probes are bound to target nucleic acids, fluorescent dyes and guanine bases of the target nucleic acids are in close proximity, and the fluorescence intensity of the fluorescent dyes is reduced by a quenching action of the guanine base.

TABLE 3

| | Base sequence |
|---|---|
| Probe for primer set c | ATCCAGAAACTAACATTCTTCTCAACGTGCCACTCC-bodipyFL (SEQ ID NO: 20) |
| Probe for primer set d | GCAAGAAGACTACACCATGAGGTGCTGAC-bodipyFL (SEQ ID NO: 28) |

A method for detecting SARS-CoV-2 virus of the present invention is a method for performing an amplification reaction through a LAMP method using the primer set of the present invention.

Enzymes used in nucleic acid synthesis are not particularly limited as long as these are template-dependent nucleic acid synthase having a strand substitution activity. Examples of such enzymes include Bst DNA polymerase (large fragment), Bca(exo-) DNA polymerase, and Klenow fragment of *Escherichia coli* DNA polymerase I, and preferably include Bst DNA polymerase (large fragment).

Reverse transcriptases used in an RT-LAMP method are not particularly limited as long as these are enzymes having an activity of synthesizing DNA using RNA as a template. Examples of such enzymes include reverse transcriptases derived from AMV, Cloned AMV, or MMLV, Superscript II, ReverTra Ace, and Thermoscript, and preferably include reverse transcriptases derived from AMV or Cloned AMV. In addition, when an enzyme, such as Bca DNA polymerase, having both a reverse transcriptase activity and a DNA polymerase activity is used, the RT-LAMP reaction can be performed with one enzyme.

Enzymes or reverse transcriptases used in nucleic acid synthesis may be purified from viruses, bacteria, or the like or may be produced by a gene recombination technique. In addition, these enzymes may be modified through, for example, fragmentation or substitution with an amino acid.

A method for testing for COVID-19 of the present invention is a method for detecting amplification of a target nucleic acid region of SARS-CoV-2 virus using the primer set of the present invention to test for presence or absence of infection with SARS-CoV-2 virus. Well-known techniques can be applied to detection of nucleic acid amplification products after a LAMP reaction. For example, the detection can be easily performed through a method in which a labeled oligonucleotide that specifically recognizes an amplified sequence or a fluorescent intercalator method (JP 2001-242169) is used or through subjecting a reaction solution after the completion of a reaction directly to agarose gel electrophoresis. In agarose gel electrophoresis, a large number of bands with different base lengths are detected in a ladder shape in LAMP amplification products. In addition, since insoluble magnesium pyrophosphate which is produced through a synthetic reaction of nucleic acids is produced in a LAMP method, a reaction solution is cloudy to the extent that it can be visually observed. A nucleic acid amplification reaction can also be detected by optically measuring such cloudiness (WO 01/83817). Furthermore, calcein, a metal indicator, can also be added to a reaction solution to detect a change in concentration of metal ions as a change in fluorescence with the progress of an amplification reaction (JP 2004-283161).

In a method for diagnosing COVID-19, the primer set of the present invention can be pre-packaged into a kit together with various reagents necessary for detecting nucleic acid amplification. Specifically, various oligonucleotides required as the primers or the loop primers of the present invention, 4 kinds of dNTPs as substrates for nucleic acid synthesis, DNA polymerases for performing nucleic acid synthesis, reverse transcriptases, buffer solutions or salts that provide suitable conditions for an enzymatic reaction, protective agents that stabilize enzymes or templates, and reagents required for detecting reaction products as necessary are provided as a kit.

EXAMPLES

Hereinafter, the present invention will be described specifically with reference to examples. However, the present invention is not limited by these examples.

Example 1. Confirmation of Detection Sensitivity of Primer Sets a and b

The detection sensitivity of a LAMP method was confirmed.
1. Preparation of Sample and Reagent
1) Sample (Transcribed RNA)
An RNA template was prepared by integrating a plasmid with cDNA prepared through RT-PCR from a SARS-CoV-2 gene and transcribing and purifying RNA from the plasmid DNA. Script Max (registered trademark) Thermo T7 Transcription Kit (manufactured by TOYOBO Co., LTD., Code Number: TSK-101) was used for the transcription, and RNeasy (registered trademark) Mini Kit (manufactured by QIAGEN N.V., Catalog Number: No. 74104) was used for RNA purification. Diluted solutions of 10 copies to $10^3$ copies per microliter were prepared from the purified RNA and used as sample solutions. In addition, a yeast RNA solution was used as a sample solution of 0 copies (negative control).
2) Concentration and Composition of Reagent Used in LAMP Method
25 µL of a LAMP reaction reagent having following composition was prepared in a 0.2 mL reagent tube. As a primer, the primer set a or b shown in Table 1 was used.
20 mM Tricine (pH 8.6),
30 mM KCl,
8 mM $MgSO_4$, 1.4 mM dNTPs,
0.5% Tween 20,
1.6 mM DTT,
1.6 µM FIP Primer and BIP Primer,
0.2 µM F3 Primer and B3 Primer,
0.8 µM Loop Primer F (LF) and Loop Primer B (LB),
AMV Reverse Transcriptase 1.0 U (20 U/µL, Manufactured by Roche Molecular Systems, Inc.),
Bst DNA polymerase 22.8 U (Manufactured by New England Biolabs),
RNase Inhibitor (40 U/µL, Manufactured by Promega) 1 µL, and
RNA template (100 copies) 5 µL.

2. Reaction by Nucleic Acid Amplification Method

1) Reaction by LAMP Method

1 µL of each of sample solutions containing 0 or 10 to $10^3$ copies of the target sequence were added to the LAMP reaction reagent prepared in 2) of 1 to obtain 25 µL of each final reaction solution. A real-time turbidity measurement device LoopampEXIA (registered trademark) was used for measurement, and the reaction conditions of 63° C. and 60 minutes were set.

3. Measurement Results

Measurement results for each of the primer sets are shown in Table 4. It was found that the number of copies that can be detected was up to 10 in the primer sets a with the N gene as a detection target and up to 50 in the primer sets b with the RdRP gene as a detection target.

TABLE 4

N Gene Use of transcribed RNA
Detection time: Minute

| Number of copies | Primer set a | | | |
|---|---|---|---|---|
| | 1 | 2 | Average value | S.D. |
| 1,000 | 16.4 | 16.2 | 16.3 | 0.14 |
| 500 | 16.5 | 16.7 | 16.6 | 0.14 |
| 200 | 18.0 | 17.7 | 17.9 | 0.21 |
| 100 | 18.4 | 17.6 | 18.0 | 0.57 |
| 50 | 23.3 | 20.2 | 21.8 | 2.19 |
| 20 | 20.1 | 23.0 | 21.6 | 2.05 |
| 10 | 25.0 | 37.3 | 31.2 | 8.70 |
| Negative control | Not detected | Not detected | | |

RdRP Gene Use of transcribed RNA
Detection time: Minute

| Number of copies | Primer set b | | | |
|---|---|---|---|---|
| | 1 | 2 | Average value | S.D. |
| 1,000 | 17.6 | 17.6 | 17.6 | 0.00 |
| 500 | 19.2 | 18.3 | 18.8 | 0.64 |
| 200 | 22.8 | 17.7 | 20.3 | 3.61 |
| 100 | 26.5 | 21.6 | 24.1 | 3.46 |
| 50 | 24.6 | 26.0 | 25.3 | 0.99 |
| 20 | Not detected | Not detected | | |
| 10 | 28.2 | Not detected | 28.2 | |
| Negative control | Not detected | Not detected | | |

Example 2. Detection Sensitivity when Genomic RNA was Used as Template

Viral genomic RNA dispensed from the National Institute of Infectious Disease was used to examine the detection sensitivity. Concurrently, PCR was also carried out for comparison of the detection sensitivity therebetween.

1. Preparation of Sample and Reagent

1) Sample (Genomic RNA)

Diluted solutions of 50 copies to $1.6 \times 10^3$ copies of genomic RNA of SARS-CoV-2 dispensed from the National Institute of Infectious Disease per microliter were prepared used as sample solutions.

2) Concentration and Composition of Reagent Used in LAMP Method

A reaction reagent was prepared in the same manner as in Example 1. The primer set a with the N gene as a detection target was used as a primer set.

3) Concentration and Composition of Reagent Used in PCR

An amplification reagent and a primer with the N gene as a detection target were prepared in accordance with "Pathogen Detection Manual 2019-nCoV Ver.2.7" of the National Institute of Infectious Disease.

2. Reaction by Nucleic Acid Amplification Method

1) Reaction by LAMP Method

An amplification reaction was carried out with a real-time turbidity measurement device LoopampEXIA (registered trademark) in the same manner as in Example 1 at 63° C. for 60 minutes.

2) Reaction by PCR

An RT-PCR method in which TaqMan probe was used was carried out in accordance with "Pathogen Detection Manual 2019-nCoV Ver.2.7" of the National Institute of Infectious Disease.

3. Measurement Results

The measurement results in each method are shown in Table 5. Although genomic RNA up to 50 copies was able to be detected in both amplification methods, the detection in the LAMP method was able to be performed in a shorter period of time than PCR.

TABLE 5

Measurement results for Genomic RNA
Detection time: Minute

LAMP Method

| Number of copies | 1 | 2 | 3 | Average value | S.D. |
|---|---|---|---|---|---|
| 1,600 | 20.3 | 19.7 | 19.3 | 19.8 | 0.5 |
| 800 | 20.0 | 19.6 | 20.2 | 19.9 | 0.3 |
| 400 | 21.2 | 21.9 | 21.6 | 21.6 | 0.4 |
| 200 | 23.2 | 25.0 | 22.7 | 23.6 | 1.2 |
| 100 | 24.7 | 26.6 | 23.1 | 24.8 | 1.8 |
| 50 | 26.3 | 26.6 | 35.9 | 29.6 | 5.5 |
| Negative control | Not detected | Not detected | Not detected | | |

Detection time: Minute

PCR

| Number of copies | 1 | 2 | 3 | Average value | S.D. |
|---|---|---|---|---|---|
| 1,600 | 29.5 | 29.6 | 29.6 | 29.6 | 0.1 |
| 800 | 30.5 | 30.7 | 30.6 | 30.6 | 0.1 |
| 400 | 31.5 | 31.5 | 31.5 | 31.5 | 0.0 |
| 200 | 32.7 | 32.5 | 32.6 | 32.6 | 0.1 |
| 100 | 33.2 | 33.5 | 34.2 | 33.6 | 0.5 |
| 50 | 34.6 | 34.7 | 35.0 | 34.8 | 0.2 |
| Negative control | Not detected | Not detected | Not detected | | |

Example 3. Confirmation of Detection Sensitivity of Primer Sets c and d

The detection sensitivity of a LAMP method was confirmed.
1. Preparation of Sample and Reagent
1) Sample (Transcribed RNA)

Artificial genes in which sequences of an M region and an S region were respectively incorporated were synthesized, and transcribed RNA copies thereof were used as templates. Synthesis of the artificial genes was outsourced to Eurofins. The sequences of the artificial genes are represented by SEQ ID NO: 29 (artificial gene for detecting M region), and SEQ ID NO: 30 (artificial gene for detecting S region).

2) Concentration and Composition of Reagent Used in LAMP Method

A LAMP reaction reagent having the following composition was prepared.

LAMP Reaction reagent:
20 mM Tricine (pH 8.6),
30 mM KCl,
0.1% Tween 20,
1.4 mM dNTPs,
8 mM MgSO$_4$,
1.6 mM DTT,
PPase 20 mU
Bst DNA polymerase 25 U,
RNase Inhibitor 1.0 U, and
AMV Reverse Transcriptase 1.0 U.

A primer set c or d, a fluorescence labeling probe corresponding to the primer set, and SYTO™ 63 Red Fluorescent Nucleic Acid Stain were added to the reaction reagent, a master mix (MM) prepared with a purified water (DW) to have a concentration of 15 µL/test was used, and a total of 25 µL including 5 µL of DW, 5 µL of a template, and the master mix was used in one reaction. The reaction reagent was prepared on ice. Master mix (amount per reaction):

LAMP Reaction reagent 12.5 µL
5 µM SYTO 0.5 µL
10 µM Probe 0.1 µL
Primer set Appropriate amount
DW Total of 15 µL.
Amount per reaction:
Master mix 15 µL
DW 5 µL
RNA template 5 µL.

2. Reaction by Nucleic Acid Amplification Method
1) Reaction by LAMP Method

A real-time quantitative PCR system LightCycler (registered trademark) 96 (manufactured by Roche Molecular Systems, Inc.) was used for measurement, and evaluation was performed at a reaction temperature of 63° C.

3. Measurement Results

Measurement results for each of the primer sets are shown in Table 6.

TABLE 6

| Number of copies | Detection time: Minute Primer set c | | | | |
|---|---|---|---|---|---|
| | 1 | 2 | 3 | 4 | Average |
| 1,000 | 6.4 | 6.5 | — | — | 6.5 |
| 50 | 12.6 | 9.6 | 10.3 | 8.9 | 10.4 |
| 25 | 10.2 | 10.8 | 9.0 | 13.1 | 10.8 |
| 12.5 | 9.8 | 12.6 | 19.3 | 11.7 | 13.4 |
| Negative control | Not detected | Not detected | — | — | — |

TABLE 6-continued

| Number of copies | Detection time: Minute Primer set d | | | | | |
|---|---|---|---|---|---|---|
| | 1 | 2 | 3 | 4 | 5 | Average |
| 1,000 | 5.9 | 5.4 | 5.7 | 5.8 | 6.0 | 5.8 |
| 100 | 6.9 | 7.8 | 6.5 | 8.2 | 7.4 | 7.4 |
| 50 | 7.4 | 8.2 | 8.9 | 8.1 | 8.1 | 8.1 |
| 25 | 9.8 | 10.0 | 12.7 | 8.3 | 8.8 | 9.9 |
| 12.5 | Not detected | 12.2 | Not detected | 10.0 | 18.1 | 13.4 |
| Negative control | Not detected | Not detected | Not detected | Not detected | Not detected | — |

The minimum detection sensitivity that could be detected within 15 minutes was 25 copies/test in any system in which any primer set was used.

Example 2. Confirmation of Cross-Reactivity with SARS Virus

At GGGenome (https://gggenome.dbcls.jp/ja/), cross-reactivity with 38 kinds of respiratory system-related bacteria and pathogenic microorganisms (Human coronavirus 229E, Human coronavirus OC43, Human coronavirus HKU1, Human coronavirus NL63, SARS-coronavirus, SARS-coronavirus-2, MERS-coronavirus, Adenovirus, Human Metapneumovirus, Parainfluenza virus 1-4, Influenza A, Influenza B, Enterovirus, Respiratory syncytial virus, Rhinovirus, *Chlamydia pneumonia, Haemophilus influenzae, Legionella pneumophila, Mycobacterium tuberculosis, Streptococcus pneumonia, Streptococcus pyrogens, Bordetella pertussis, Mycoplasma pneumoniae, Pneumocystis jirovecii* (PJP), Influenza C, Parechovirus, *Candida albicans, Corynebacterium diphtheriae, Legionella* non-*pneumophila, Bacillus anthracosis* (Anthrax), *Moraxella cararrhalis, Neisseria elongate* and *miningitidis, Pseudomonas aeruginosa, Staphylococcus epidermis, Staphylococcus salivarius*, Leptospirosis, *Chlamydia psittaci, Coxiella burneti* (Q-Fever), *Streptococcus aureus*) was confirmed in silico for each of the M region and the S region.

As a result, in only an M region of SARS-Coronavirus (SARS virus), a mismatch in a probe design region was within 5 bases and each of mismatches in F1, F2, B1, and B2 primer design regions was within 3 bases, and these became positions for a LAMP reaction. Therefore, the cross-reactivity with SARS virus was confirmed.

Transcribed RNA of an artificial gene with which a sequence of SARS virus (GenBank NC004718.3) having high homology for each region was integrated was used as a template of the SARS virus (synthesis request destination: Eurofins Scientific). The amount of template was $1.0 \times 10^7$ copies/test.

Measurement results for each of the primer sets are shown in Table 7.

TABLE 7

Detection time: Minute

| | Primer set c | | | | |
|---|---|---|---|---|---|
| Template | 1 | 2 | 3 | 4 | Average |
| $1 \times 10^7$ Copies of SARS | Not detected | Not detected | Not detected | Not detected | — |
| 1,000 Copies of SARS-CoV-2 | 5.6 | 5.6 | — | — | 5.6 |
| Negative control | Not detected | Not detected | — | — | — |

Detection time: Minute

| | Primer set d | | | | |
|---|---|---|---|---|---|
| Template | 1 | 2 | 3 | 4 | Average |
| $1 \times 10^7$ Copies of SARS | Not detected | Not detected | Not detected | Not detected | — |
| 1,000 Copies of SARS-CoV-2 | 5.7 | 5.7 | — | — | 5.7 |
| Negative control | Not detected | Not detected | — | — | — |

No cross-reaction with SARS virus was observed in both detection systems. In addition, assuming a case of co-infection with SARS-CoV-2 and SARS virus, tests in which $1.0 \times 10^6$ copies/test of transcribed RNA of SARS virus was mixed with 25 or 1,000 copies/test of transcribed RNA of SARS-CoV-2 were performed.

Measurement results for each of the primer sets are shown in Table 8.

TABLE 8

Detection time: Minute

| Template | | Primer set c | | | |
|---|---|---|---|---|---|
| | | 1 | 2 | 3 | Average |
| 1,000 Copies of SARS-CoV-2 | $1 \times 10^6$ Copies of SARS | 5.2 | 5.2 | 5.1 | 5.2 |
| | No SARS | 5.2 | 5.2 | 5.3 | 5.2 |
| 25 Copies of SARS-CoV-2 | $1 \times 10^6$ Copies of SARS | 6.7 | 7.9 | 7.2 | 7.3 |
| | No SARS | 6.9 | 7.5 | 6.9 | 7.1 |
| Negative control | | Not detected | Not detected | Not detected | — |

Detection time: Minute

| Template | | Primer set d | | | |
|---|---|---|---|---|---|
| | | 1 | 2 | 3 | Average |
| 1,000 Copies of SARS-CoV-2 | $1 \times 10^6$ Copies of SARS | 5.4 | 5.5 | 5.4 | 5.4 |
| | No SARS | 5.5 | 5.5 | 5.6 | 5.5 |
| 25 Copies of SARS-CoV-2 | $1 \times 10^6$ Copies of SARS | 7.8 | 9.9 | 10.0 | 9.2 |
| | No SARS | 11.3 | 10.3 | 12.3 | 11.3 |
| Negative control | | Not detected | Not detected | Not detected | — |

SARS-CoV-2 could also be detected in the mixing test.

The invention claimed is:

1. A primer set for detecting SARS-CoV-2 virus through amplification by a LAMP method,
wherein the primer set consists of at least one selected from the group consisting of (c1) and (d1):
(c1) a primer set consisting of an F3 primer consisting of SEQ ID NO: 14, a B3 primer consisting of SEQ ID NO: 15, an FIP primer consisting of SEQ ID NO: 16, and a BIP primer consisting of SEQ ID NO: 17; and
(d1) a primer set consisting of an F3 primer consisting of SEQ ID NO: 21, a B3 primer consisting of SEQ ID NO: 22, a B4 primer consisting of SEQ ID NO: 23, an FIP primer consisting of SEQ ID NO: 24, and a BIP primer consisting of SEQ ID NO: 25.

2. A primer set for detecting SARS-CoV-2 virus through amplification by a LAMP method,
wherein the primer set consists of at least one selected from the group consisting of (c2) and (d2):
(c2) a primer set consisting of an F3 primer consisting of SEQ ID NO: 14, a B3 primer consisting of SEQ ID NO: 15, an FIP primer consisting of SEQ ID NO: 16, a BIP primer consisting of SEQ ID NO: 17, an LF primer consisting of SEQ ID NO: 18, and an LB primer consisting of SEQ ID NO: 19; and
(d2) a primer set consisting of an F3 primer consisting of SEQ ID NO: 21, a B3 primer consisting of SEQ ID NO: 22, a B4 primer consisting of SEQ ID NO: 23, an FIP primer consisting of SEQ ID NO: 24, a BIP primer consisting of SEQ ID NO: 25, an LF primer consisting of SEQ ID NO: 26, and an LB primer consisting of SEQ ID NO: 27.

3. A kit for detecting SARS-CoV-2 virus through amplification by a LAMP method, comprising:
the primer set of claim 1; and
a fluorescence labeling probe.

4. The kit of claim 3,
wherein
the fluorescence labeling probe is a probe consisting of SEQ ID NO: 20.

5. The kit of claim 3, which is used for testing for COVID-19.

6. A method for detecting SARS-CoV-2 virus, comprising:
performing an amplification reaction through a LAMP method using the primer set of claim 1.

7. A method for testing for COVID-19, comprising:
detecting amplification of a target nucleic acid region of SARS-CoV-2 virus using the primer set of claim 1 to test for presence or absence of infection with SARS-CoV-2 virus.

8. A method for detecting SARS-CoV-2 virus, comprising:
performing an amplification reaction through a LAMP method using the kit of claim 3.

9. A method for testing for COVID-19, comprising:
detecting amplification of a target nucleic acid region of SARS-CoV-2 virus using the kit of claim 3 to test for presence or absence of infection with SARS-CoV-2 virus.

10. A kit for detecting SARS-CoV2 virus through amplification by a LAMP method, comprising:
the primer set of claim 2; and
a fluorescence labeling probe.

11. The kit of claim 10,
wherein the fluorescence labeling probe is a probe consisting of SEQ ID NO: 20.

12. The kit of claim 10, which is used for testing for COVID-19.

13. A method for detecting SARS-CoV-2 virus, comprising:
performing an amplification reaction through a LAMP method using the primer set of claim 2.

14. A method for testing for COVID-19, comprising:
detecting amplification of a target nucleic acid region of SARS-CoV-2 virus using the primer set of claim 2 to test for presence or absence of infection with SARS-CoV-2 virus.

15. A method for detecting SARS-CoV-2 virus, comprising:
performing an amplification reaction through a LAMP method using the kit of claim 10.

16. A method for testing for COVID-19, comprising:
detecting amplification of a target nucleic acid region of SARS-CoV-2 virus using the kit of claim 10 to test for presence or absence of infection with SARS-CoV-2 virus.

* * * * *

SEQUENCE LISTING

```
<160> NUMBER OF SEQ ID NOS: 30

<210> SEQ ID NO 1
<211> LENGTH: 29903
<212> TYPE: DNA
<213> ORGANISM: SARS-CoV-2

<400> SEQUENCE: 1
attaaaggtt  tataccttcc  caggtaacaa  accaaccaac  tttcgatctc  ttgtagatct     60
gttctctaaa  cgaactttaa  aatctgtgtg  gctgtcactc  ggctgcatgc  ttagtgcact    120
cacgcagtat  aattaataac  taattactgt  cgttgacagg  acacgagtaa  ctcgtctatc    180
ttctgcaggc  tgcttacggt  ttcgtccgtg  ttgcagccga  tcatcagcac  atctaggttt    240
cgtccgggtg  tgaccgaaag  gtaagatgga  gagccttgtc  cctggtttca  acgagaaaac    300
acacgtccaa  ctcagtttgc  ctgttttaca  ggttcgcgac  gtgctcgtac  gtggctttgg    360
agactccgtg  gaggaggtct  tatcagaggc  acgtcaacat  cttaaagatg  gcacttgtgg    420
cttagtagaa  gttgaaaaag  gcgttttgcc  tcaacttgaa  cagccctatg  tgttcatcaa    480
acgttcggat  gctcgaactg  cacctcatgg  tcatgttatg  gttgagctgg  tagcagaact    540
cgaaggcatt  cagtacggtc  gtagtggtga  gacacttggt  gtccttgtcc  ctcatgtggg    600
cgaaatacca  gtggcttacc  gcaaggttct  tcttcgtaag  aacggtaata  aaggagctgg    660
tggccatagt  tacggcgccg  atctaaagtc  atttgactta  ggcgacgagc  ttggcactga    720
tccttatgaa  gattttcaag  aaaactggaa  cactaaacat  agcagtggtg  ttacccgtga    780
```

```
actcatgcgt gagcttaacg gagggcata cactcgctat gtcgataaca acttctgtgg    840 cctgatggc tacctcttg agtgcattaa agaccttcta gcacgtgctg gtaaagcttc    900
atgcactttg tccgaacaac tggactttat tgacactaag aggggtgtat actgctgccg    960
tgaacatgag catgaaattg cttggtacac ggaacgttct gaaaagagct atgaattgca    1020
gacacctttt gaaattaaat tggcaaagaa atttgacacc ttcaatgggg aatgtccaaa    1080
ttttgtattt ccctttaaatt ccataatcaa gactattcaa ccaaggggttg aaaagaaaaa    1140 gcttgatggc tttatgggta gaattcgatc tgtctatcca gttgcgtcac caaatgaatg    1200
caaccaaatg tgccttcaa ctctcatgaa gtgtgatcat tgtggtgaaa cttcatggca    1260
gacgggcgat tttgttaaag ccacttgcga attttgtggc actgagaatt tgactaaaga    1320
aggtgccact acttgtggtt acttaccca aaatgctgtt gttaaattt attgtccagc    1380 atgtcacaat tcagaagtag gacctgagca tagtcttgcc gaataccata tgaatctgg    1440 cttgaaaacc attcttcgta agggtggtcg cactattgcc tttggaggct gtgtgttctc    1500
ttatgttggt tgccataaca agtgtgccta tgggttcca cgtgctagcg ctaacatagg    1560
ttgtaaccat acaggtgttg ttggagaagg ttccgaaggt cttaatgaca accttcttga    1620
aatactccaa aaagagaaag tcaacatcaa tattgttggt gactttaaac ttaatgaaga    1680
gatcgccatt attttggcat cttttctgc ttccacaagt gcttttgtgg aaactgtgaa    1740
aggtttggat tataaagcat tcaaacaaat tgttgaatcc tgtggtaatt ttaaagttac    1800
aaaaggaaaa gctaaaaaag gtgcctggaa tattggtgaa cagaaatcaa tactgagtcc    1860
tctttatgca tttgcatcag aggctgctcg tgttgtacga tcaattttct cccgcactct    1920
tgaaactgct caaaattctg tgcgtgtttt acagaaggcc gctataacaa tactagatgg    1980
aatttcacag tattcactga gactcattga tgctatgatg ttcacatctg atttggctac    2040
taacaatcta gttgtaatgg cctacattac aggtggtgtt gttcagttga cttcgcagtg    2100
gctaactaac atctttggca ctgtttatga aaaactcaaa cccgtcttg attggcttga    2160 agagaagttt aaggaaggtg tagagtttct tagagacggt tgggaaattg ttaatttat    2220 ctcaacctgt gcttgtgaaa ttgtcggtgg acaaattgtc acctgtgcaa aggaaattaa    2280
ggagagtgtt cagacattct ttaagcttgt aaataaattt ttggctttgt gtgctgactc    2340
tatcattatt ggtggagcta aacttaaagc cttgaatta ggtgaaacat tgtcacgca    2400 ctcaaaggga ttgtacagaa agtgtgttaa atccagagaa gaaactggcc tactcatgcc    2460
tctaaaagcc ccaaaagaaa ttatcttctt agagggagaa acacttccca cagaagtgtt    2520
aacagaggaa gttgtcttga aaactggtga tttacaacca ttagaacaac ctactagtga    2580
agctgttgaa gctccattgg ttggtacacc agtttgtatt aacgggctta tgttgctcga    2640
aatcaaagac acagaaaagt actgtgccct tgcacctaat atgatggtaa caaacaatac    2700
cttcacactc aaaggcggtg caccaacaaa ggttacttt ggtgatgaca ctgtgataga    2760
agtgcaaggt tacaagagtg tgaatatcac ttttgaactt gatgaaagga ttgataaagt    2820
acttaatgag aagtgctctg cctatacagt tgaactcggt acagaagtaa atgagttcgc    2880
ctgtgttgtg gcagatgctg tcataaaaac tttgcaacca gtatctgaat tacttacacc    2940
actgggcatt gatttagatg agtggagtat ggctacatac tacttattg atgagtctgg    3000 tgagtttaaa ttggcttcac atatgtattg ttctttctac cctccagatg aggatgaaga    3060
agaaggtgat tgtgaagaag aagagttga gccatcaact caatatgagt atggtactga    3120
agatgattac caaggtaaac ctttggaatt tggtgccact tctgctgctc ttcaacctga    3180
```

```
agaagagcaa gaagaagatt ggttagatga tgatagtcaa caaactgttg gtcaacaaga   3240
cggcagtgag gacaatcaga caactactat tcaaacaatt gttgaggttc aacctcaatt   3300
agagatggaa cttacaccag ttgttcagac tattgaagtg aatagtttta gtggttattt   3360
aaaacttact gacaatgtat acattaaaaa tgcagacatt gtggaagaag ctaaaaaggt   3420
aaaaccaaca gtggttgtta atgcagccaa tgtttacctt aaacatggag gaggtgttgc   3480
aggagcctta aataaggcta ctaacaatgc catgcaagtt gaatctgatg attacatagc   3540
tactaatgga ccacttaaag tgggtggtag ttgtgtttta agcggacaca atcttgctaa   3600
acactgtctt catgttgtcg gcccaaatgt taacaaaggt gaagacattc aacttcttaa   3660
gagtgcttat gaaaatttta atcagcacga agttctactt gcaccattat tatcagctgg   3720 tattttggt gctgacccta tacattcttt aagagtttgt gtagatactg ttcgcacaaa   3780
tgtctactta gctgtctttg ataaaaatct ctatgacaaa cttgtttcaa gcttttttgga   3840 aatgaagagt gaaaagcaag ttgaacaaaa gatcgctgag attcctaaag aggaagttaa   3900 gccattata actgaaagta aaccttcagt tgaacagaga aaacaagatg ataagaaaat   3960
caaagcttgt gttgaagaag ttacaacaac tctggaagaa actaagttcc tcacagaaaa   4020
cttgttactt tatattgaca ttaatggcaa tcttcatcca gattctgcca ctcttgttag   4080
tgacattgac atcactttct aaagaaaga tgctccatat atagtgggtg atgttgttca   4140
agagggtgtt ttaactgctg tggttatacc tactaaaaag gctggtggca ctactgaaat   4200
gctagcgaaa gctttgagaa agtgccaac agacaattat ataaccactt acccgggtca   4260
gggtttaaat ggttacactg tagaggaggc aaagacagtg cttaaaaagt gtaaaagtgc   4320
cttttacatt ctaccatcta ttatctctaa tgagaagcaa gaaattcttg gaactgtttc   4380
ttggaatttg cgagaaatgc ttgcacatgc agaagaaaca cgcaaattaa tgcctgtctg   4440
tgtgaaaact aaagccatag tttcaactat acagcgtaaa tataagggta ttaaaataca   4500
agagggtgtg gttgattatg gtgctagatt ttactttac accagtaaaa caactgtagc   4560
gtcacttatc aacacactta acgatctaaa tgaaactctt gttacaatgc cacttggcta   4620
tgtaacacat ggcttaaatt tggaagaagc tgctcggtat atgagatctc tcaaagtgcc   4680
agctacagtt tctgtttctt cacctgatgc tgttacagcg tataatggtt atcttacttc   4740
ttcttctaaa acacctgaag aacatttat tgaaccatc tcacttgctg gttcctataa   4800
agattggtcc tattctggac aatctacaca actaggtata gaatttctta agagaggtga   4860
taaaagtgta tattcactca gtaatcctac cacattccac ctagatggtg aagttatcac   4920
ctttgacaat cttaagacac ttctttcttt gagagaagtg aggactatta aggtgtttac   4980
aacagtagac aacattaacc tccacacgca agttgtggac atgtcaatga catatggaca   5040
acagtttggt ccaacttatt tggatggagc tgatgttact aaaataaaac ctcataattc   5100
acatgaaggt aaaacatttt atgttttacc taatgatgac actctacgtg ttgaggcttt   5160
tgagtactac cacacaactg atcctagttt tctgggtagg tacatgtcag cattaaatca   5220
cactaaaaag tggaaatacc acaagttaa tggtttaact tctattaaat gggcagataa   5280
caactgttat cttgccactg cattgttaac actccaacaa atagagttga gtttaatcc   5340 acctgctcta caagatgctt attacagagc aagggctggt gaagctgcta acttttgtgc   5400
acttatctta gcctactgta ataagacagt aggtgagtta ggtgatgtta gagaaacaat   5460
gagttacttg tttcaacatg ccaatttaga ttcttgcaaa agagtcttga acgtggtgtg   5520
```

-continued

```
taaaacttgt ggacaacagc agacaaccct aagggtgta gaagctgtta tgtacatggg    5580
cacactttct tatgaacaat ttaagaaagg tgttcagata ccttgtacgt gtggtaaaca    5640
agctacaaaa tatctagtac aacaggagtc accttttgtt atgatgtcag caccacctgc    5700
tcagtatgaa cttaagcatg gtacatttac ttgtgctagt gagtacactg gtaattacca    5760
gtgtggtcac tataaacata aacttctaa agaaactttg tattgcatag acggtgcttt    5820
acttacaaag tcctcagaat acaaaggtcc tattacggat gttttctaca agaaaacag    5880
ttacacaaca accataaaac cagttactta taaattggat ggtgttgttt gtacagaaat    5940
tgaccctaag ttggacaatt attataagaa agacaattct tatttcacag agcaaccaat    6000
tgatcttgta ccaaaccaac catatccaaa cgcaagcttc gataatttta gtttgtatg    6060
tgataatatc aaatttgctg atgatttaaa ccagttaact ggtttataaga aacctgcttc    6120
aagagagctt aaagttacat ttttccctga cttaaatggt gatgtggtgg ctattgatta    6180
taaacactac acaccctctt ttaagaaagg agctaaattg ttacataaac ctattgtttg    6240
gcatgttaac aatgcaacta ataaagccac gtataaacca ataccggt gtacgttg    6300
tctttggagc acaaaaccag ttgaaacatc aaattcgttt gatgtactga agtcagagga    6360
cgcgcaggga atggataatc ttgcctgcga agatctaaaa ccagtctctg aagaagtagt    6420
ggaaaatcct accatacaga aagacgttct tgagtgtaat gtgaaaacta ccgaagttgt    6480
aggagacatt atacttaaac cagcaaataa tagtttaaaa attacagaag aggttggcca    6540
cacagatcta atggctgctt atgtagacaa ttctagtctt actattaaga aacctaatga    6600
attatctaga gtattaggtt tgaaaaccct tgctactcat ggtttagctg ctgttaatag    6660
tgtcccttgg gatactatag ctaattatgc taagcctttt cttaacaaag ttgttagtac    6720
aactactaac atagttacac ggtgtttaaa ccgtgtttgt actaattata tgccttattt    6780
ctttacttta ttgctacaat tgtgtactt tactagaagt acaaattcta gaattaaagc    6840
atctatgccg actactatag caaagaatac tgttaagagt gtcggtaaat tttgtctaga    6900
ggcttcattt aattatttga agtcacctaa ttttctaaa ctgataaata ttataatttg    6960
gttttactta ttaagtgttt gcctaggttc tttaatctac tcaaccgctg ctttaggtgt    7020
tttaatgtct aatttaggca tgccttctta ctgtactggt tacagagaag gctatttgaa    7080
ctctactaat gtcactattg caacctactg tactggttct ataccttgta gtgtttgtct    7140
tagtggttta gattctttag acacctatcc ttctttagaa actatacaaa ttaccatttc    7200
atcttttaaa tgggatttaa ctgcttttgg cttagttgca gagtggttt tggcatatat    7260
tcttttcact aggttttct atgtacttgg attggctgca atcatgcaat tgttttcag    7320
ctattttgca gtacatttta ttagtaattc ttggcttatg tggttaataa ttaatcttgt    7380
acaaatggcc ccgatttcag ctatggttag aatgtacatc ttctttgcat cattttatta    7440
tgtatggaaa agttatgtgc atgttgtaga cggttgtaat tcatcaactt gtatgatgtg    7500
ttacaaacgt aatagagcaa caagagtcga atgtacaact attgttaatg gtgttagaag    7560
gtccttttat gtctatgcta atggaggtaa aggcttttgc aaactacaca attggaattg    7620
tgttaattgt gatacattct gtgctggtag tacatttatt agtgatgaag ttgcgagaga    7680
cttgtcacta cagtttaaaa gaccaataaa tcctactgac cagtcttctt acatcgttga    7740
tagtgttaca gtgaagaatg gttccatcca tctttacttt gataaagctg gtcaaaagac    7800
ttatgaaaga cattctctct ctcatttgt taacttagac aacctgagag ctaataacac    7860
taaaggttca ttgcctatta atgttatagt ttttgatggt aaatcaaat gtgaagaatc    7920
```

```
atctgcaaaa tcagcgtctg tttactacag tcagcttatg tgtcaaccta tactgttact   7980
agatcaggca ttagtgtctg atgttggtga tagtgcggaa gttgcagtta aaatgtttga   8040
tgcttacgtt aatacgtttt catcaacttt taacgtacca atggaaaaac tcaaaacact   8100
agttgcaact gcagaagctg aacttgcaaa gaatgtgtcc ttagacaatg tcttatctac   8160
tttttatttca gcagctcggc aagggtttgt tgattcagat gtagaaacta agatgttgt    8220
tgaatgtctt aaattgtcac atcaatctga catagaagtt actggcgata gttgtaataa   8280
ctatatgctc acctataaca aagttgaaaa catgacaccc cgtgaccttg gtgcttgtat   8340
tgactgtagt gcgcgtcata ttaatgcgca ggtagcaaaa agtcacaaca ttgctttgat   8400
atggaacgtt aaagatttca tgtcattgtc tgaacaacta cgaaaacaaa tacgtagtgc   8460
tgctaaaaag aataacttac ctttaagtt gacatgtgca actactagac aagttgttaa    8520
tgttgtaaca acaaagatag cacttaaggg tggtaaaatt gttaataatt ggttgaagca   8580
gttaattaaa gttacacttg tgttcctttt tgttgctgct attttctatt taataacacc   8640
tgttcatgtc atgtctaaac atactgactt tcaagtgaa atcataggat acaaggctat    8700
tgatggtggt gtcactcgtg acatagcatc tacagatact tgttttgcta acaaacatgc   8760
tgattttgac acatggttta gccagcgtgg tggtagttat actaatgaca aagcttgccc   8820
attgattgct gcagtcataa caagagaagt gggttttgtc gtgcctggtt tgcctggcac   8880
gatattacgc acaactaatg gtgactttt gcatttctta cctagagttt ttagtgcagt    8940
tggtaacatc tgttcacac catcaaaact tatagagtac actgactttg caacatcagc    9000
ttgtgttttg gctgctgaat gtacaatttt taaagatgct tctggtaagc cagtaccata   9060
ttgttatga accaatgtac tagaaggttc tgttgcttat gaaagtttac gccctgacac   9120
acgttatgtg ctcatggatg gctctattat tcaatttcct aacacctacc ttgaaggttc   9180
tgttagagtg gtaacaactt ttgattctga gtactgtagg cacggcactt gtgaaagatc   9240
agaagctggt gtttgtgtat ctactagtgg tagatgggta cttaacaatg attattacag   9300
atctttacca ggagttttct gtggtgtaga tgctgtaaat ttacttacta atatgtttac   9360
accactaatt caacctattg gtgctttga catatcagca tctatagtag ctggtggtat   9420
tgtagctatc gtagtaacat gccttgccta ctattttatg aggtttagaa gagcttttgg   9480
tgaatacagt catgtagttg cctttaatac tttactattc cttatgtcat tcactgtact   9540
ctgtttaaca ccagtttact cattcttacc tggtgtttat tctgttattt acttgtactt   9600
gacattttat cttactaatg atgtttcttt tttagcacat attcagtgga tggttatgtt   9660
cacacccttta gtacctttct ggataacaat tgcttatatc atttgtattt ccacaaagca   9720
tttctattgg ttcttagta attacctaaa gagacgtgta gtctttaatg gtgtttcctt   9780
tagtactttt gaagaagctg cgctgtgcac ctttttgtta aataaagaaa tgtatctaaa   9840
gttgcgtagt gatgtgctat tacctcttac gcaatataat agatacttag ctctttataa   9900
taagtacaag tattttagtg gagcaatgga tacaactagc tacagagaag ctgcttgttg   9960
tcatctcgca aaggctctca atgacttcag taactcaggt tctgatgttc tttaccaacc   10020
accacaaacc tctatcacct cagctgtttt gcagagtggt tttagaaaaa tggcattccc   10080
atctggtaaa gttgagggtt gtatggtaca agtaacttgt ggtacaacta cacttaacgg   10140
tctttggctt gatgacgtag tttactgtcc aagacatgtg atctgcacct ctgaagacat   10200
gcttaaccct aattatgaag atttactcat tcgtaagtct aatcataatt tcttggtaca   10260
```

```
ggctggtaat gttcaactca gggttattgg acattctatg caaaattgtg tacttaagct    10320
taaggttgat acagccaatc ctaagacacc taagtataag tttgttcgca ttcaaccagg    10380
acagactttt tcagtgttag cttgttacaa tggttcacca tctggtgttt accaatgtgc    10440
tatgaggccc aatttcacta ttaagggttc attccttaat ggttcatgtg gtagtgttgg    10500
ttttaacata gattatgact gtgtctcttt ttgttacatg caccatatgg aattaccaac    10560
tggagttcat gctggcacag acttagaagg taacttttat ggacctttg ttgacaggca    10620 aacagcacaa gcagctggta cggacacaac tattacagtt aatgttttag cttggttgta    10680
cgctgctgtt ataaatggag acaggtggtt tctcaatcga tttaccacaa ctcttaatga    10740
ctttaacctt gtggctatga agtacaatta tgaacctcta acacaagacc atgttgacat    10800
actaggacct ctttctgctc aaactggaat tgccgtttta gatatgtgtg cttcattaaa    10860
agaattactg caaaatggta tgaatggacg taccatattg ggtagtgctt tattagaaga    10920
tgaatttaca ccttttgatg ttgttagaca atgctcaggt gttactttcc aaagtgcagt    10980
gaaaagaaca atcaagggta cacaccactg gttgttactc acaattttga cttcactttt    11040
agttttagtc cagagtactc aatggtcttt gttctttttt ttgtatgaaa atgcctttt     11100 accttttgct atgggtatta ttgctatgtc tgcttttgca atgatgtttg tcaaacataa    11160
gcatgcattt ctctgtttgt ttttgttacc ttctcttgcc actgtagctt attttaatat    11220
ggtctatatg cctgctagtt gggtgatgcg tattatgaca tggttggata tggttgatac    11280
tagtttgtct ggttttaagc taaaagactg tgttatgtat gcatcagctg tagtgttact    11340
aatccttatg acagcaagaa ctgtgtatga tgatggtgct aggagagtgt ggacacttat    11400
gaatgtcttg acactcgttt ataaagttta ttatggtaat gctttagatc aagccatttc    11460
catgtgggct cttataatct ctgttacttc taactactca ggtgtagtta caactgtcat    11520 gttttttggcc agaggtattg ttttatgtg tgttgagtat tgccctattt tcttcataac    11580
tggtaataca cttcagtgta taatgctagt ttattgtttc ttaggctatt tttgtacttg    11640
ttactttggc ctcttttgtt tactcaaccg ctactttaga ctgactcttg gtgtttatga    11700
ttacttagtt tctacacagg agtttagata tatgaattca cagggactac tcccacccaa    11760
gaatagcata gatgccttca aactcaacat taaattgttg ggtgttggtg gcaaaccttg    11820
tatcaaagta gccactgtac agtctaaaat gtcagatgta aagtgcacat cagtagtctt    11880
actctcagtt ttgcaacaac tcagagtaga atcatcatct aaattgtggg ctcaatgtgt    11940
ccagttacac aatgacattc tcttagctaa agatactact gaagcctttg aaaaaatggt    12000
ttcactactt tctgtttttgc tttccatgca gggtgctgta gacataaaca agctttgtga    12060
agaaatgctg gacaacaggg caaccttaca agctatagcc tcagagttta gttcccttcc    12120
atcatatgca gcttttgcta ctgctcaaga agcttatgag caggctgttg ctaatggtga    12180
ttctgaagtt gttcttaaaa agttgaagaa gtctttgaat gtggctaaat ctgaatttga    12240
ccgtgatgca gccatgcaac gtaagttgga aaagatggct gatcaagcta tgacccaaat    12300
gtataaacag gctagatctg aggacaagag ggcaaaagtt actagtgcta tgcagacaat    12360
gcttttcact atgcttagaa agttggataa tgatgcactc aacaacatta tcaacaatgc    12420
aagagatggt tgtgttccct tgaacataat acctcttaca acagcagcca actaatggtt    12480
tgtcatacca gactataaca catataaaaa tacgtgtgat ggtacaacat ttacttatgc    12540
atcagcattg tgggaaatcc aacaggttgt agatgcagat agtaaaattg ttcaacttag    12600
tgaaattagt atggacaatt cacctaattt agcatggcct cttattgtaa cagctttaag    12660
```

```
ggccaattct gctgtcaaat tacagaataa tgagcttagt cctgttgcac tacgacagat    12720
gtcttgtgct gccggtacta cacaaactgc ttgcactgat gacaatgcgt tagcttacta    12780
caacacaaca aagggaggta ggtttgtact tgcactgtta tccgatttac aggatttgaa    12840
atgggctaga ttccctaaga gtgatggaac tggtactatc tatacagaac tggaaccacc    12900
ttgtaggttt gttacagaca cacctaaagg tcctaaagtg aagtatttat actttattaa    12960
aggattaaac aacctaaata gaggtatggt acttggtagt ttagctgcca cagtacgtct    13020
acaagctggt aatgcaacag aagtgcctgc caattcaact gtattatctt tctgtgcttt    13080
tgctgtagat gctgctaaag cttacaaaga ttatctagct agtgggggac aaccaatcac    13140
taattgtgtt aagatgttgt gtacacacac tggtactggt caggcaataa cagttacacc    13200
ggaagccaat atggatcaag aatcctttgg tggtgcatcg tgttgtctgt actgccgttg    13260
ccacatagat catccaaatc ctaaaggatt ttgtgactta aaaggtaagt atgtacaaat    13320
acctacaact tgtgctaatg accctgtggg ttttacactt aaaaacacag tctgtaccgt    13380
ctgcggtatg tggaaaggtt atggctgtag ttgtgatcaa ctccgcgaac ccatgcttca    13440
gtcagctgat gcacaatcgt ttttaaacgg gtttgcggtg taagtgcagc ccgtcttaca    13500
ccgtgcggca caggcactag tactgatgtc gtatacaggg cttttgacat ctacaatgat    13560
aaagtagctg ttttgctaa attcctaaaa actaattgtt gtcgcttcca agaaaaggac    13620
gaagatgaca atttaattga ttcttacttt gtagttaaga gacacacttt ctctaactac    13680
caacatgaag aaacaattta taatttactt aaggattgtc cagctgttgc taaacatgac    13740
ttctttaagt ttagaataga cggtgacatg gtaccacata tatcacgtca acgtcttact    13800
aaatacacaa tggcagacct cgtctatgct ttaaggcatt ttgatgaagg taattgtgac    13860
acattaaaag aaatacttgt cacatacaat tgttgtgatg atgattattt caataaaaag    13920
gactggtatg attttgtaga aaacccagat atattacgcg tatacgccaa cttaggtgaa    13980
cgtgtacgcc aagctttgtt aaaaacagta caattctgtg atgccatgcg aaatgctggt    14040
attgttggtg tactgacatt agataatcaa gatctcaatg gtaactggta tgatttcggt    14100
gatttcatac aaaccacgcc aggtagtgga gttcctgttg tagattctta ttattcattg    14160
ttaatgccta tattaacctt gaccagggct ttaactgcag agtcacatgt tgacactgac    14220
ttaacaaagc cttacattaa gtgggatttg ttaaaatatg acttcacgga agagaggtta    14280
aaactctttg accgttattt taaatattgg gatcagacat accacccaaa ttgtgttaac    14340
tgtttggatg acagatgcat tctgcattgt gcaaacttta atgttttatt ctctacagtg    14400
ttcccaccta caagttttgg accactagtg agaaaaatat tgttgatgg tgttccattt    14460 gtagtttcaa ctggatacca cttcagagag ctaggtgttg tacataatca ggatgtaaac    14520
ttacatagct ctagacttag ttttaaggaa ttacttgtgt atgctgctga ccctgctatg    14580
cacgctgctt ctggtaatct attactagat aaacgcacta cgtgcttttc agtagctgca    14640
cttactaaca atgttgcttt tcaaactgtc aaacccggta attttaacaa agacttctat    14700
gactttgctg tgtctaaggg ttttcttaag gaaggaagtt ctgttgaatt aaaaacacttc    14760 ttctttgctc aggatggtaa tgctgctatc agcgattatg actactatcg ttataatcta    14820
ccaacaatgt gtgatatcag acaactacta tttgtagttg aagttgttga taagtacttt    14880
gattgttacg atggtggctg tattaatgct aaccaagtca tcgtcaacaa cctagacaaa    14940
tcagctggtt ttccatttaa taaatgggt aaggctagac tttattatga ttcaatgagt    15000
```

```
tatgaggatc aagatgcact tttcgcatat acaaaacgta atgtcatccc tactataact    15060
caaatgaatc ttaagtatgc cattagtgca aagaatagag ctcgcaccgt agctggtgtc    15120
tctatctgta gtactatgac caatagacag tttcatcaaa aattattgaa atcaatagcc    15180
gccactagag gagctactgt agtaattgga acaagcaaat tctatggtgg ttggcacaac    15240
atgttaaaaa ctgtttatag tgatgtagaa aaccctcacc ttatgggttg ggattatcct    15300
aaatgtgata gagccatgcc taacatgctt agaattatgg cctcacttgt tcttgctcgc    15360
aaacatacaa cgtgttgtag cttgtcacac cgtttctata gattagctaa tgagtgtgct    15420
caagtattga gtgaaatggt catgtgtggc ggttcactat atgttaaacc aggtggaacc    15480
tcatcaggag atgccacaac tgcttatgct aatagtgttt ttaacatttg tcaagctgtc    15540
acggccaatg ttaatgcact tttatctact gatggtaaca aaattgccga taagtatgtc    15600
cgcaatttac aacacagact ttatgagtgt ctctatagaa atagagatgt tgacacagac    15660
tttgtgaatg agttttacgc atatttgcgt aaacatttct caatgatgat actctctgac    15720
gatgctgttg tgtgtttcaa tagcacttat gcatctcaag gtctagtggc tagcataaag    15780
aactttaagt cagttcttta ttatcaaaac aatgttttta tgtctgaagc aaaatgttgg    15840
actgagactg accttactaa aggacctcat gaattttgct ctcaacatac aatgctagtt    15900
aaacagggtg atgattatgt gtaccttcct tacccagatc catcaagaat cctaggggcc    15960
ggctgttttg tagatgatat cgtaaaaaca gatggtacac ttatgattga acggttcgtg    16020
tctttagcta tagatgctta cccacttact aaacatccta atcaggagta tgctgatgtc    16080
tttcatttgt acttacaata cataagaaag ctacatgatg agttaacagg acacatgtta    16140
gacatgtatt ctgttatgct tactaatgat aacacttcaa ggtattggga acctgagttt    16200
tatgaggcta tgtacacacc gcatacagtc ttacaggctg ttggggcttg tgttctttgc    16260
aattcacaga cttcattaag atgtggtgct tgcatacgta gaccattctt atgttgtaaa    16320
tgctgttacg accatgtcat atcaacatca cataaattag tcttgtctgt taatccgtat    16380
gtttgcaatg ctccaggttg tgatgtcaca gatgtgactc aactttactt aggaggtatg    16440
agctattatt gtaaatcaca taaaccaccc attagttttc cattgtgtgc taatggacaa    16500 gttttttggtt tatataaaaa tacatgtgtt ggtagcgata atgttactga ctttaatgca    16560
attgcaacat gtgactggac aaatgctggt gattacattt tagctaacac ctgtactgaa    16620
agactcaagc ttttttgcagc agaaacgctc aaagctactg aggagacatt taaactgtct    16680
tatggtattg ctactgtacg tgaagtgctg tctgacagag aattacatct ttcatgggaa    16740
gttggtaaac ctagaccacc acttaaccga attatgtct ttactggtta tcgtgtaact    16800
aaaaacagta aagtacaaat aggagagtac acctttgaaa aaggtgacta tggtgatgct    16860
gttgtttacc gaggtacaac aacttacaaa ttaaatgttg gtgattattt tgtgctgaca    16920
tcacatacag taatgccatt aagtgcacct acactagtgc cacaagagca ctatgttaga    16980
attactggct tatacccaac actcaatatc tcagatgagt tttctagcaa tgttgcaaat    17040
tatcaaaagg ttggtatgca aaagtattct cactccagg gaccacctgg tactggtaag    17100
agtcattttg ctattggcct agctctctac taccctcttc gtcgcatagt gtatacagct    17160
tgctctcatg ccgctgttga tgcactatgt gagaaggcat taaatatttt gcctatagat    17220
aaatgtagta gaattatacc tgcacgtgct cgtgtagagt gttttgataa attcaaagtg    17280
aattcaacat tagaacagta tgtcttttgt actgtaaatg cattgccctga gacgacagca    17340 gatatagttg tctttgatga aatttcaatg gccacaaatt atgatttgag tgttgtcaat    17400
```

```
gccagattac gtgctaagca ctatgtgtac attggcgacc ctgctcaatt acctgcacca    17460
cgcacattgc taactaaggg cacactagaa ccagaatatt tcaattcagt gtgtagactt    17520
atgaaaacta taggtccaga catgttcctc ggaacttgtc ggcgttgtcc tgctgaaatt    17580
gttgacactg tgagtgcttt ggtttatgat aataagctta aagcacataa agacaaatca    17640
gctcaatgct ttaaaatgtt ttataagggt gttatcacgc atgatgtttc atctgcaatt    17700
aacaggccac aaataggcgt ggtaagagaa ttccttacac gtaaccctgc ttggagaaaa    17760
gctgtcttta tttcacctta taattcacag aatgctgtag cctcaaagat tttgggacta    17820
ccaactcaaa ctgttgattc atcacagggc tcagaatatg actatgtcat attcactcaa    17880
accactgaaa cagctcactc ttgtaatgta aacagattta atgttgctat taccagagca    17940
aaagtaggca tactttgcat aatgtctgat agagaccttt atgacaagtt gcaatttaca    18000
agtcttgaaa ttccacgtag gaatgtggca actttacaag ctgaaaatgt aacaggactc    18060
tttaaagatt gtagtaaggt aatcactggg ttacatccta cacaggcacc tacacacctc    18120
agtgttgaca ctaaattcaa aactgaaggt ttatgtgttg acatacctgg catacctaag    18180
gacatgacct atagaagact catctctatg atgggtttta aaatgaatta tcaagttaat    18240
ggttacccta acatgtttat cacccgcgaa gaagctataa gacatgtacg tgcatggatt    18300
ggcttcgatg tcgaggggtg tcatgctact agagaagctg ttggtaccaa tttacctttg    18360
cagctaggtt tttctacagg tgttaaccta gttgctgtac ctacaggtta tgttgataca    18420
cctaataata cagattttc cagagttagt gctaaaccac cgcctggaga tcaatttaaa    18480
cacctcatac cacttatgta caaggacttc ccttggaatg tagtgcgtat aaagattgta    18540
caaatgttaa gtgacacact taaaaatctc tctgacagag tcgtatttgt cttatgggca    18600
catggctttg agttgacatc tatgaagtat tttgtgaaaa taggacctga gcgcacctgt    18660
tgtctatgtg atagacgtgc cacatgcttt tccactgctt cagacactta tgcctgttgg    18720
catcattcta ttggatttga ttacgtctat aatccgttta tgattgatgt tcaacaatgg    18780
ggttttacag gtaacctaca aagcaaccat gatctgtatt gtcaagtcca tggtaatgca    18840
catgtagcta gttgtgatgc aatcatgact aggtgtctag ctgtccacga gtgctttgtt    18900
aagcgtgttg actggactat tgaatatcct ataattggtg atgaactgaa gattaatgcg    18960
gcttgtagaa aggttcaaca catggttgtt aaagctgcat tattagcaga caaattccca    19020
gttcttcacg acattggtaa ccctaaagct attaagtgtg tacctcaagc tgatgtagaa    19080
tggaagttct atgatgcaca gccttgtagt gacaaagctt ataaaataga agaattattc    19140
tattcttatg ccacacattc tgacaaattc acagatggtg tatgcctatt ttggaattgc    19200
aatgtcgata gatatcctgc taattccatt gtttgtagat ttgacactag agtgctatct    19260
aaccttaact tgcctggttg tgatggtggc agtttgtatg taaataaaca tgcattccac    19320
acaccagctt ttgataaaag tgcttttgtt aatttaaaac aattaccatt tttctattac    19380
tctgacagtc catgtgagtc tcatggaaaa caagtagtgt cagatataga ttatgtacca    19440
ctaaagtctg ctacgtgtat aacacgttgc aatttaggtg gtgctgtctg tagacatcat    19500
gctaatgagt acagattgta tctcgatgct tataacatga tgatctcagc tggctttagc    19560
ttgtgggttt acaaacaatt tgatacttat aacctctgga acacttttac aagacttcag    19620
agtttagaaa atgtggcttt taatgttgta aataagggac actttgatgg acaacagggt    19680
gaagtaccag tttctatcat taataacact gtttacacaa aagttgatgg tgttgatgta    19740
```

```
gaattgtttg aaaataaaac aacattacct gttaatgtag catttgagct ttgggctaag    19800
cgcaacatta aaccagtacc agaggtgaaa atactcaata atttgggtgt ggacattgct    19860
gctaatactg tgatctggga ctacaaaaga gatgctccag cacatatatc tactattggt    19920
gtttgttcta tgactgacat agccaagaaa ccaactgaaa cgatttgtgc accactcact    19980
gtcttttttg atggtagagt tgatggtcaa gtagacttat ttagaaatgc ccgtaatggt    20040
gttcttatta cagaaggtag tgttaaaggt ttacaaccat ctgtaggtcc caaacaagct    20100
agtcttaatg gagtcacatt aattggagaa gccgtaaaaa cacagttcaa ttattataag    20160
aaagttgatg gtgttgtcca acaattacct gaaacttact ttactcagag tagaaattta    20220
caagaattta acccaggagt tcaaatggaa attgatttct tagaattagc tatggatgaa    20280
ttcattgaac ggtataaatt agaaggctat gccttcgaac atatcgttta tggagatttt    20340
agtcatagtc agttaggtgg tttacatcta ctgattggac tagctaaacg ttttaaggaa    20400 tcacctttttg aattagaaga ttttattcct atggacagta cagttaaaaa ctatttcata    20460
acagatgcgc aaacaggttc atctaagtgt gtgtgttctg ttattgattt attacttgat    20520
gattttgttg aaataataaa atcccaagat ttatctgtag tttctaaggt tgtcaaagtg    20580
actattgact atacagaaat tcatttatg ctttggtgta aagatggcca tgtagaaaca    20640
ttttacccaa aattacaatc tagtcaagcg tggcaaccgg tgttgctat gcctaatctt    20700 tacaaaatgc aaagaatgct attagaaaag tgtgaccttc aaaattatgg tgatagtgca    20760
acattaccta aaggcataat gatgaatgtc gcaaaatata ctcaactgtg tcaatattta    20820
aacacattaa cattagctgt acccta taat atgagagtta cattttgg tgctggttct    20880 gataaaggag ttgcaccagg tacagctgtt taagacagt ggttgcctac gggtacgctg    20940
cttgtcgatt cagatcttaa tgactttgtc tctgatgcag attcaactt gattggtgat    21000 tgtgcaactg tacatacagc taataaatgg gatctcatta ttagtgatat gtacgaccct    21060
aagactaaaa atgttacaaa agaaaatgac tctaaagagg gttttttcac ttacatttgt    21120
gggtttatac aacaaaagct agctcttgga ggttccgtgg ctataaagat aacagaacat    21180
tcttggaatg ctgatcttta taagctcatg ggacacttcg catggtggac agcctttgtt    21240
actaatgtga atgcgtcatc atctgaagca ttttttaattg gatgtaatta tcttggcaaa    21300
ccacgcgaac aaatagatgg ttatgtcatg catgcaaatt acatattttg gaggaataca    21360
aatccaattc agttgtcttc ctattctttta tttgacatga gtaaatttcc ccttaaatta    21420
aggggtactg ctgttatgtc tttaaaagaa ggtcaaatca atgatatgat tttatctctt    21480
cttagtaaag gtagacttat aattagagaa aacaacagag ttgttattc tagtgatgtt    21540 cttgttaaca ctaaacgaa caatgtttgt ttttcttgtt ttattgccac tagtctctag    21600
tcagtgtgtt aatcttacaa ccagaactca attaccccct gcatacacta attctttcac    21660
acgtggtgtt tattaccctg acaaagtttt cagatcctca gttttacatt caactcagga    21720
cttgttctta cctttctttt ccaatgttac ttggttccat gctatacatg tctctgggac    21780
caatggtact aagaggtttg ataaccctgt cctaccattt aatgatggtg tttattttgc    21840
ttccactgag aagtctaaca taataagagg ctggattttt ggtactactt tagattcgaa    21900
gacccagtcc ctacttattg ttaataacgc tactaatgtt gttattaaag tctgtgaatt    21960 tcaatttttgt aatgatccat ttttgggtgt ttattaccac aaaaacaaca aaagttggat    22020
ggaaagtgag ttcagagttt attctagtgc gaataattgc acttttgaat atgtctctca    22080
gccttttctt atgaccttg aaggaaaaca gggtaatttc aaaaatctta gggaatttgt    22140
```

```
gtttaagaat attgatggtt attttaaaat atattctaag cacacgccta ttaatttagt   22200
gcgtgatctc cctcagggtt tttcggcttt agaaccattg gtagatttgc caataggtat   22260
taacatcact aggtttcaaa ctttacttgc tttacataga agttatttga ctcctggtga   22320
ttcttcttca ggttggacag ctggtgctgc agcttattat gtgggttatc ttcaacctag   22380
gacttttcta ttaaaatata atgaaaatgg aaccattaca gatgctgtag actgtgcact   22440
tgaccctctc tcagaaacaa agtgtacgtt gaaatccttc actgtagaaa aaggaatcta   22500
tcaaacttct aactttagag tccaaccaac agaatctatt gttagatttc ctaatattac   22560
aaacttgtgc cctttggtg aagttttaa cgccaccaga tttgcatctg tttatgcttg   22620
gaacaggaag agaatcagca actgtgttgc tgattattct gtcctatata attccgcatc   22680
attttccact tttaagtgtt atggagtgtc tcctactaaa ttaaatgatc tctgctttac   22740
taatgtctat gcagattcat ttgtaattag aggtgatgaa gtcagacaaa tcgctccagg   22800
gcaaactgga aagattgctg attataatta taaattacca gatgatttta caggctgcgt   22860
tatagcttgg aattctaaca atcttgattc taaggttggt ggtaattata attacctgta   22920
tagattgttt aggaagtcta atctcaaacc ttttgagaga gatatttcaa ctgaaatcta   22980
tcaggccggt agcacacctt gtaatggtgt tgaaggtttt aattgttact tcctttaca   23040 atcatatggt ttccaaccca ctaatggtgt tggttaccaa ccatacagag tagtagtact   23100
ttcttttgaa cttctacatg caccagcaac tgtttgtgga cctaaaaagt ctactaattt   23160
ggttaaaaac aaatgtgtca atttcaactt caatggttta acaggcacag gtgttcttac   23220
tgagtctaac aaaaagtttc tgcctttcca acaatttggc agagacattg ctgacactac   23280
tgatgctgtc cgtgatccac agacacttga gattcttgac attacaccat gttcttttgg   23340
tggtgtcagt gttataacac aggaacaaa tacttctaac caggttgctg ttctttatca   23400
ggatgttaac tgcacagaag tccctgttgc tattcatgca gatcaactta ctcctacttg   23460
gcgtgtttat tctacaggtt ctaatgtttt tcaaacacgt gcaggctgtt aatagggc   23520 tgaacatgtc aacaactcat atgagtgtga catacccatt ggtgcaggta tatgcgctag   23580
ttatcagact cagactaatt ctcctcggcg ggcacgtagt gtagctagtc aatccatcat   23640
tgcctacact atgtcacttg gtgcagaaaa ttcagttgct tactctaata actctattgc   23700
catacccaca aattttacta ttagtgttac cacagaaatt ctaccagtgt ctatgaccaa   23760
gacatcagta gattgtacaa tgtacatttg tggtgattca actgaatgca gcaatctttt   23820
gttgcaatat ggcagttttt gtacacaatt aaaccgtgct ttaactggaa tagctgttga   23880
acaagacaaa aacacccaag aagttttgc acaagtcaaa caaatttaca aaacaccacc   23940
aattaaagat tttggtggtt ttaattttc acaaatatta ccagatccat caaaaccaag   24000
caagaggtca tttattgaag atctactttt caacaaagtg acacttgcag atgctggctt   24060
catcaaacaa tatggtgatt gccttggtga tattgctgct agagacctca tttgtgcaca   24120
aaagtttaac ggccttactg ttttgccacc tttgctcaca gatgaaatga ttgctcaata   24180
cacttctgca ctgttagcgg gtacaatcac ttctggttgg acctttggtg caggtgctgc   24240
attacaaata ccatttgcta tgcaaatggc ttataggttt aatggtattg gagttacaca   24300
gaatgttctc tatgagaacc aaaaattgat tgccaaccaa tttaatagtg ctattggcaa   24360
aattcaagac tcactttctt ccacagcaag tgcacttgga aaacttcaag atgtggtcaa   24420
ccaaaatgca caagctttaa acacgcttgt taaacaactt agctccaatt ttggtgcaat   24480
```

```
ttcaagtgtt ttaaatgata tcctttcacg tcttgacaaa gttgaggctg aagtgcaaat    24540
tgataggttg atcacaggca gacttcaaag tttgcagaca tatgtgactc aacaattaat    24600
tagagctgca gaaatcagag cttctgctaa tcttgctgct actaaaatgt cagagtgtgt    24660
acttggacaa tcaaaaagag ttgattttg tggaagggc tatcatctta tgtccttccc    24720
tcagtcagca cctcatggtg tagtcttctt gcatgtgact tatgtccctg cacaagaaaa    24780
gaacttcaca actgctcctg ccatttgtca tgatggaaaa gcacactttc ctcgtgaagg    24840
tgtctttgtt tcaaatggca cacactggtt tgtaacacaa aggaattttt atgaaccaca    24900
aatcattact acagacaaca catttgtgtc tggtaactgt gatgttgtaa taggaattgt    24960
caacaacaca gtttatgatc ctttgcaacc tgaattagac tcattcaagg aggagttaga    25020
taaatatttt aagaatcata catcaccaga tgttgattta ggtgacatct ctggcattaa    25080
tgcttcagtt gtaaacattc aaaaagaaat tgaccgcctc aatgaggttg ccaagaattt    25140
aaatgaatct ctcatcgatc tccaagaact tggaaagtat gagcagtata taaaatggcc    25200
atggtacatt tggctaggtt ttatagctgg cttgattgcc atagtaatgg tgacaattat    25260
gctttgctgt atgaccagtt gctgtagtta tctcaagggc tgttgttctt gtggatcctg    25320
ctgcaaattt gatgaagacg actctgagcc agtgctcaaa ggagtcaaat tacattacac    25380
ataaacgaac ttatggattt gtttatgaga atcttcacaa ttggaactgt aactttgaag    25440
caaggtgaaa tcaaggatgc tactccttca gattttgttc gcgctactgc aacgataccg    25500
atacaagcct cactcccttt cggatggctt attgttggcg ttgcacttct tgctgttttt    25560
cagagcgctt ccaaaatcat aaccctcaaa aagagatggc aactagcact ctccaagggt    25620
gttcactttg tttgcaactt gctgttgttg tttgtaacag tttactcaca cctttgctc    25680 gttgctgctg gccttgaagc ccctttctc tatctttatg ctttagtcta cttcttgcag    25740
agtataaact ttgtaagaat aataatgagg ctttggcttt gctggaaatg ccgttccaaa    25800
aacccattac tttatgatgc caactatttt cttgctggc atactaattg ttacgactat    25860
tgtatacctt acaatagtgt aacttcttca attgtcatta cttcaggtga tggcacaaca    25920
agtcctattt ctgaacatga ctaccagatt ggtggttata ctgaaaaatg ggaatctgga    25980
gtaaaagact gtgttgtatt acacagttac ttcacttcag actattacca gctgtactca    26040
actcaattga gtacagacac tggtgttgaa catgttacct tcttcatcta caataaaatt    26100
gttgatgagc ctgaagaaca tgtccaaatt cacacaatcg acggttcatc cggagttgtt    26160
aatccagtaa tggaaccaat ttatgatgaa ccgacgacga ctactagcgt gccttttgtaa    26220 gcacaagctg atgagtacga acttatgtac tcattcgttt cggaagagac aggtacgtta    26280
atagttaata gcgtacttct ttttcttgct ttcgtggtat tcttgctagt tacactagcc    26340
atccttactg cgcttcgatt gtgtgcgtac tgctgcaata ttgttaacgt gagtcttgta    26400
aaaccttctt tttacgttta ctctcgtgtt aaaaatctga attcttctag agttcctgat    26460
cttctggtct aaacgaacta atattatat tagttttct gtttggaact ttaatttag    26520 ccatggcaga ttccaacggt actattaccg ttgaagagct aaaaagctc cttgaacaat    26580 ggaacctagt aataggttc ctattcctta catggatttg tcttctacaa tttgcctatg    26640
ccaacaggaa taggttttg tatataatta agttaattt cctctggctg ttatggccag    26700
taactttagc ttgttttgtg cttgctgctg tttacagaat aaattggatc accggtggaa    26760
ttgctatcgc aatggcttgt cttgtaggct tgatgtggct cagctacttc attgcttctt    26820
tcagactgtt tgcgcgtacg cgttccatgt ggtcattcaa tccagaaact aacattcttc    26880
```

```
tcaacgtgcc actccatggc actattctga ccagaccgct tctagaaagt gaactcgtaa  26940
tcggagctgt gatccttcgt ggacatcttc gtattgctgg acaccatcta ggacgctgtg  27000
acatcaagga cctgcctaaa gaaatcactg ttgctacatc acgaacgctt tcttattaca  27060
aattgggagc ttcgcagcgt gtagcaggtg actcaggttt tgctgcatac agtcgctaca  27120
ggattggcaa ctataaatta aacacagacc attccagtag cagtgacaat attgctttgc  27180
ttgtacagta agtgacaaca gatgtttcat ctcgttgact ttcaggttac tatagcagag  27240
atattactaa ttattatgag gacttttaaa gtttccattt ggaatcttga ttacatcata  27300
aacctcataa ttaaaaattt atctaagtca ctaactgaga ataaatattc tcaattagat  27360
gaagagcaac caatggagat tgattaaacg aacatgaaaa ttattctttt cttggcactg  27420
ataacactcg ctactgtga gctttatcac taccaagagt gtgttagagg tacaacagta  27480
cttttaaaag aaccttgctc ttctggaaca tacgagggca attcaccatt tcatcctcta  27540
gctgataaca aatttgcact gacttgcttt agcactcaat ttgcttttgc ttgtcctgac  27600
ggcgtaaaac acgtctatca gttacgtgcc agatcagttt cacctaaact gttcatcaga  27660
caagaggaag ttcaagaact ttactctcca attttcctta ttgttgcggc aatagtgttt  27720
ataacacttt gcttcacact caaaagaaag acagaatgat tgaactttca ttaattgact  27780
tctatttgtg ctttttagcc tttctgctat tccttgtttt aattatgctt attatctttt  27840
ggttctcact tgaactgcaa gatcataatg aaacttgtca cgcctaaacg aacatgaaat  27900
ttcttgtttt cttaggaatc atcacaactg tagctgcatt tcaccaagaa tgtagtttac  27960
agtcatgtac tcaacatcaa ccatatgtag ttgatgaccc gtgtcctatt cacttctatt  28020
ctaaatggta tattagagta ggagctagaa aatcagcacc tttaattgaa ttgtgcgtgg  28080
atgaggctgg ttctaaatca cccattcagt acatcgatat cggtaattat acagtttcct  28140
gtttaccttt tacaattaat tgccaggaac ctaaattggg tagtcttgta gtgcgttgtt  28200
cgttctatga agactttta gagtatcatg acgttcgtgt tgttttagat ttcatctaaa  28260
cgaacaaact aaaatgtctg ataatggacc ccaaaatcag cgaaatgcac cccgcattac  28320
gtttggtgga ccctcagatt caactggcag taaccagaat ggagaacgca gtggggcgcg  28380
atcaaaacaa cgtcggcccc aaggtttacc caataatact gcgtcttggt tcaccgctct  28440
cactcaacat ggcaaggaag accttaaatt ccctcgagga caaggcgttc aattaacac   28500 caatagcagt ccagatgacc aaattggcta ctaccgaaga gctaccagac gaattcgtgg  28560
tggtgacggt aaaatgaaag atctcagtcc aagatggtat ttctactacc taggaactgg  28620
gccagaagct ggacttccct atggtgctaa caaagacggc atcatatggg ttgcaactga  28680
gggagccttg aatacaccaa agatcacat tggcacccgc aatcctgcta acaatgctgc  28740
aatcgtgcta caacttcctc aaggaacaac attgccaaaa ggcttctacg cagaagggag  28800
cagaggcgga agtcaagcct cttctcgttc ctcatcacgt agtcgcaaca gttcaagaaa  28860
ttcaactcca ggcagcagta ggggaacttc tcctgctaga atggctggca atggcggtga  28920
tgctgctctt gctttgctgc tgcttgacag attgaaccag cttgagagca aaatgtctgg  28980
taaaggccaa caacaacaag gccaaactgt cactaagaaa tctgctgctg aggcttctaa  29040
gaagcctcgg caaaaacgta ctgccactaa agcatacaat gtaacacaag ctttcggcag  29100
acgtggtcca gaacaaaccc aaggaaattt tggggaccag gaactaatca gacaaggaac  29160
tgattacaaa cattggccgc aaattgcaca atttgccccc agcgcttcag cgttcttcgg  29220
```

-continued

```
aatgtcgcgc attggcatgg aagtcacacc ttcgggaacg tggttgacct acacaggtgc    29280
catcaaattg gatgacaaag atccaaattt caaagatcaa gtcatttgc tgaataagca     29340 tattgacgca tacaaaacat tcccaccaac agagcctaaa aaggacaaaa agaagaaggc    29400
tgatgaaact caagccttac cgcagagaca aagaaacag caaactgtga ctcttcttcc    29460
tgctgcagat ttggatgatt tctccaaaca attgcaacaa tccatgagca gtgctgactc    29520
aactcaggcc taaactcatg cagaccacac aaggcagatg ggctatataa acgttttcgc    29580
ttttccgttt acgatatata gtctactctt gtgcagaatg aattctcgta actacatagc    29640
acaagtagat gtagttaact ttaatctcac atagcaatct ttaatcagtg tgtaacatta    29700
gggaggactt gaaagagcca ccacattttc accgaggcca cgcggagtac gatcgagtgt    29760
acagtgaaca atgctaggga gagctgccta tatggaagag ccctaatgtg taaaattaat    29820
tttagtagtg ctatccccat gtgattttaa tagcttctta ggagaatgac aaaaaaaaaa    29880
aaaaaaaaaa aaaaaaaaaa aaa                                            29903
```

```
<210> SEQ ID NO 2
<211> LENGTH: 19
<212> TYPE: DNA
<213> ORGANISM: Artificial Sequence
<220> FEATURE:
<223> OTHER INFORMATION: F3 primer

<400> SEQUENCE: 2
tctggtaaag gccaacaac                                                 19

<210> SEQ ID NO 3
<211> LENGTH: 14
<212> TYPE: DNA
<213> ORGANISM: Artificial Sequence
<220> FEATURE:
<223> OTHER INFORMATION: B3 primer

<400> SEQUENCE: 3
gctgaagcgc tggg                                                      14

<210> SEQ ID NO 4
<211> LENGTH: 36
<212> TYPE: DNA
<213> ORGANISM: Artificial Sequence
<220> FEATURE:
<223> OTHER INFORMATION: FIP primer

<400> SEQUENCE: 4
agtacgtttt tgccgaggca aggccaaact gtcact                              36

<210> SEQ ID NO 5
<211> LENGTH: 39
<212> TYPE: DNA
<213> ORGANISM: Artificial Sequence
<220> FEATURE:
<223> OTHER INFORMATION: BIP primer

<400> SEQUENCE: 5
gtaacacaag ctttcggcag attagttcct ggtccccaa                           39

<210> SEQ ID NO 6
<211> LENGTH: 17
<212> TYPE: DNA
<213> ORGANISM: Artificial Sequence
<220> FEATURE:
<223> OTHER INFORMATION: LF primer
```

-continued

```
<400> SEQUENCE: 6
aagcctcagc agcagat                                              17

<210> SEQ ID NO 7
<211> LENGTH: 18
<212> TYPE: DNA
<213> ORGANISM: Artificial Sequence
<220> FEATURE:
<223> OTHER INFORMATION: LB primer

<400> SEQUENCE: 7
tccagaacaa acccaagg                                             18

<210> SEQ ID NO 8
<211> LENGTH: 24
<212> TYPE: DNA
<213> ORGANISM: Artificial Sequence
<220> FEATURE:
<223> OTHER INFORMATION: F3 primer

<400> SEQUENCE: 8
ttctatagat tagctaatga gtgt                                      24

<210> SEQ ID NO 9
<211> LENGTH: 22
<212> TYPE: DNA
<213> ORGANISM: Artificial Sequence
<220> FEATURE:
<223> OTHER INFORMATION: B3 primer

<400> SEQUENCE: 9
acttatcggc aattttgtta cc                                        22

<210> SEQ ID NO 10
<211> LENGTH: 46
<212> TYPE: DNA
<213> ORGANISM: Artificial Sequence
<220> FEATURE:
<223> OTHER INFORMATION: FIP primer

<400> SEQUENCE: 10
gaggttccac ctggtttaac atatctcaag tattgagtga aatggt              46

<210> SEQ ID NO 11
<211> LENGTH: 46
<212> TYPE: DNA
<213> ORGANISM: Artificial Sequence
<220> FEATURE:
<223> OTHER INFORMATION: BIP primer

<400> SEQUENCE: 11
caggagatgc cacaactgct tatagataaa agtgcattaa cattgg              46

<210> SEQ ID NO 12
<211> LENGTH: 18
<212> TYPE: DNA
<213> ORGANISM: Artificial Sequence
<220> FEATURE:
<223> OTHER INFORMATION: LF primer

<400> SEQUENCE: 12
gaaccgccac acatgacc                                             18

<210> SEQ ID NO 13
```

```
<211> LENGTH: 20
<212> TYPE: DNA
<213> ORGANISM: Artificial Sequence
<220> FEATURE:
<223> OTHER INFORMATION: LB primer

<400> SEQUENCE: 13
catttgtcaa gctgtcacgg                                                20

<210> SEQ ID NO 14
<211> LENGTH: 18
<212> TYPE: DNA
<213> ORGANISM: Artificial Sequence
<220> FEATURE:
<223> OTHER INFORMATION: F3 primer

<400> SEQUENCE: 14
tcgcaatggc ttgtcttg                                                  18

<210> SEQ ID NO 15
<211> LENGTH: 20
<212> TYPE: DNA
<213> ORGANISM: Artificial Sequence
<220> FEATURE:
<223> OTHER INFORMATION: B3 primer

<400> SEQUENCE: 15
gcaatacgaa gatgtccacg                                                20

<210> SEQ ID NO 16
<211> LENGTH: 33
<212> TYPE: DNA
<213> ORGANISM: Artificial Sequence
<220> FEATURE:
<223> OTHER INFORMATION: FIP primer

<400> SEQUENCE: 16
cgtacgcgca aacagtggct tgatgtggct cag                                 33

<210> SEQ ID NO 17
<211> LENGTH: 37
<212> TYPE: DNA
<213> ORGANISM: Artificial Sequence
<220> FEATURE:
<223> OTHER INFORMATION: BIP primer

<400> SEQUENCE: 17
cgttccatgt ggtcattcat agaagcggtc tggtcag                             37

<210> SEQ ID NO 18
<211> LENGTH: 20
<212> TYPE: DNA
<213> ORGANISM: Artificial Sequence
<220> FEATURE:
<223> OTHER INFORMATION: LF primer

<400> SEQUENCE: 18
gaaagaagca atgaagtagc                                                20

<210> SEQ ID NO 19
<211> LENGTH: 22
<212> TYPE: DNA
<213> ORGANISM: Artificial Sequence
<220> FEATURE:
<223> OTHER INFORMATION: LB primer

<400> SEQUENCE: 19
```
gaaactaaca ttcttctcaa cg                                                22

<210> SEQ ID NO 20
<211> LENGTH: 36
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (36)..(36)
<220> FEATURE:
<221> NAME/KEY: misc_feature
<222> LOCATION: (36)..(36)
<223> OTHER INFORMATION: bodipy FL

<400> SEQUENCE: 20
atccagaaac taacattctt ctcaacgtgc cactcc                                  36

<210> SEQ ID NO 21
<211> LENGTH: 23
<212> TYPE: DNA
<213> ORGANISM: Artificial Sequence
<220> FEATURE:
<223> OTHER INFORMATION: F3 primer

<400> SEQUENCE: 21
tacttggaca atcaaaaaga gtt                                               23

<210> SEQ ID NO 22
<211> LENGTH: 24
<212> TYPE: DNA
<213> ORGANISM: Artificial Sequence
<220> FEATURE:
<223> OTHER INFORMATION: B3 primer

<400> SEQUENCE: 22
gtctgtagta atgatttgtg gttc                                              24

<210> SEQ ID NO 23
<211> LENGTH: 22
<212> TYPE: DNA
<213> ORGANISM: Artificial Sequence
<220> FEATURE:
<223> OTHER INFORMATION: B4 primer

<400> SEQUENCE: 23
tgtctgtagt aatgatttgt gg                                                22

<210> SEQ ID NO 24
<211> LENGTH: 42
<212> TYPE: DNA
<213> ORGANISM: Artificial Sequence
<220> FEATURE:
<223> OTHER INFORMATION: FIP primer

<400> SEQUENCE: 24
cttttcttgt gcagggacac tatcatctta tgtccttccc tc                           42

<210> SEQ ID NO 25
<211> LENGTH: 38
<212> TYPE: DNA
<213> ORGANISM: Artificial Sequence
<220> FEATURE:
<223> OTHER INFORMATION: BIP primer

<400> SEQUENCE: 25

-continued

```
tcacaactgc tcctgcctga aacaaagaca ccttcacg                    38
```

<210> SEQ ID NO 26
<211> LENGTH: 21
<212> TYPE: DNA
<213> ORGANISM: Artificial Sequence
<220> FEATURE:
<223> OTHER INFORMATION: LF primer

<400> SEQUENCE: 26

```
acatgcaaga agactacacc a                                      21
```

<210> SEQ ID NO 27
<211> LENGTH: 21
<212> TYPE: DNA
<213> ORGANISM: Artificial Sequence
<220> FEATURE:
<223> OTHER INFORMATION: LB primer

<400> SEQUENCE: 27

```
gatggaaaag cacactttcc t                                      21
```

<210> SEQ ID NO 28
<211> LENGTH: 29
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (29)..(29)
<223> OTHER INFORMATION: bodipy FL

<400> SEQUENCE: 28

```
gcaagaagac tacaccatga ggtgctgac                              29
```

<210> SEQ ID NO 29
<211> LENGTH: 377
<212> TYPE: DNA
<213> ORGANISM: Artificial Sequence
<220> FEATURE:
<223> OTHER INFORMATION: Artificial Sequnce for detecting SARS-CoV-2 M
      region

<400> SEQUENCE: 29

```
gtaatacgac tcactatagg gatggccagt aactttagct tgttttgtgc ttgctgctgt    60
ttacagaata aattggatca ccggtggaat tgctatcgca atggcttgtc ttgtaggctt   120
gatgtggctc agctacttca ttgcttcttt cagactgttt gcgcgtacgc gttccatgtg   180
gtcattcaat ccagaaacta acattcttct caacgtgcca ctccatggca ctattctgac   240
cagaccgctt ctagaaagtg aactcgtaat cggagctgtg atccttcgtg gacatcttcg   300
tattgctgga caccatctag gacgctgtga catcaaggac ctgcctaaag aaatcactgt   360
tgctacatca cgaacgc                                                  377
```

<210> SEQ ID NO 30
<211> LENGTH: 1593
<212> TYPE: DNA
<213> ORGANISM: Artificial Sequence
<220> FEATURE:
<223> OTHER INFORMATION: Artificial Sequnce for detecting SARS-CoV-2 S2
      region

<400> SEQUENCE: 30

```
gtaatacgac tcactatagg gaatctttty ttgcaatatg gcagtttttg tacacaatta    60
aaccgtgctt taactggaat agctgttgaa caagacaaaa acacccaaga agttttttgca   120 caagtcaaac aaatttacaa acaccacca attaaagatt ttggtggttt taattttttca   180 caaatattac cagatccatc aaaaccaagc aagaggtcat ttattgaaga tctacttttc   240
aacaaagtga cacttgcaga tgctggcttc atcaaacaat atggtgattg ccttggtgat   300
attgctgcta gagacctcat ttgtgcacaa aagtttaacg gccttactgt tttgccacct   360
ttgctcacag atgaaatgat tgctcaatac acttctgcac tgttagcggg tacaatcact   420
tctggttgga cctttggtgc aggtgctgca ttacaaatac catttgctat gcaaatggct   480
tataggttta atggtattgg agttacacag aatgttctct atgagaacca aaaattgatt   540
gccaaccaat ttaatagtgc tattggcaaa attcaagact cactttcttc cacagcaagt   600
gcacttggaa aacttcaaga tgtggtcaac caaaatgcac aagctttaaa cacgcttgtt   660
aaacaactta gctccaattt tggtgcaatt tcaagtgttt taaatgatat cctttcacgt   720
cttgacaaag ttgaggctga agtgcaaatt gataggttga tcacaggcag acttcaaagt   780
ttgcagacat atgtgactca acaattaatt agagctgcag aaatcagagc ttctgctaat   840
cttgctgcta ctaaaatgtc agagtgtgta cttggacaat caaaaagagt tgattttttgt   900 ggaaagggct atcatcttat gtccttccct cagtcagcac ctcatggtgt agtcttcttg   960
catgtgactt atgtccctgc acaagaaaag aacttcacaa ctgctcctgc catttgtcat  1020
gatggaaaag cacactttcc tcgtgaaggt gtctttgttt caaatggcac acactggttt  1080
gtaacacaaa ggaattttta tgaaccacaa atcattacta cagacaacac atttgtgtct  1140
ggtaactgtg atgttgtaat aggaattgtc aacaacacag tttatgatcc tttgcaacct  1200
gaattagact cattcaagga ggagttagat aaatatttta agaatcatac atcaccagat  1260
gttgatttag gtgacatctc tggcattaat gcttcagttg taaacattca aaaagaaatt  1320
gaccgcctca atgaggttgc caagaattta aatgaatctc tcatcgatct ccaagaactt  1380
ggaaagtatg agcagtatat aaaatggcca tggtacattt ggctaggttt tatagctggc  1440
ttgattgcca tagtaatggt gacaattatg ctttgctgta tgaccagttg ctgtagttgt  1500
ctcaagggct gttgttcttg tggatcctgc tgcaaatttg atgaagacga ctctgagcca  1560
gtgctcaaag gagtcaaatt acattacaca taa                                1593
```